(12) United States Patent
Sauer et al.

(10) Patent No.: US 7,422,889 B2
(45) Date of Patent: Sep. 9, 2008

(54) DRE RECOMBINASE AND RECOMBINASE SYSTEMS EMPLOYING DRE RECOMBINASE

(75) Inventors: Brian L. Sauer, Kansas City, MO (US); Jeffrey McDermott, Mission, KS (US)

(73) Assignee: Stowers Institute for Medical Research, Kansas City, MO (US)

(*) Notice: Subject to any disclaimer, the term of this patent is extended or adjusted under 35 U.S.C. 154(b) by 381 days.

(21) Appl. No.: 11/025,511

(22) Filed: Dec. 29, 2004

(65) Prior Publication Data

US 2006/0094029 A1   May 4, 2006

Related U.S. Application Data

(60) Provisional application No. 60/623,701, filed on Oct. 29, 2004.

(51) Int. Cl.
*C12N 9/22* (2006.01)
*C12N 15/55* (2006.01)

(52) U.S. Cl. .................. 435/199; 435/194; 536/23.2

(58) Field of Classification Search ............ None
See application file for complete search history.

(56) References Cited

OTHER PUBLICATIONS

Brukner, I., et al., "Sequence-dependent bending propensity of DNA as revealed by DNase I: parameters for trinucleotides", *EMBO J* (1995) pp. 1812-1818, vol. 14. No. 8.
Lobocka, M.B., et al., "Genome of Bacteriophage P1", *J Bacteriology* (2004) pp. 7032-7068. vol. 186, No. 21.
Sauer, B., "Chromosome Manipulation by Cre-lox Recombination", *Mobile DNA II* (2002) Ch. 4, pp. 38-58, ASM Press, Washington, D.C., (Craig, N.L., Craigie, R., Gellert, M., and Lambowitz, A. M., eds).
Watkins, C.A., et al., "Characterization of Bacteriophage D6", *Virology* (1981) pp. 302-317, vol. 110.
Altschul, S.F., et al., "Gapped BLAST and PSI-BLAST: a new generation of protein database search programs", *Nucleic Acids Res.* (1997) pp. 3389-3402, vol. 25.
Argos, P., et al., "The Integrase family of site-specific recombinases: regional similarities and global diversity", *EMBO J.* (1986) pp. 433-440, vol. 5.
Austin, S., et al., "A Novel Role for Site-Specific Recombination in Maintenance of Bacterial Replicons", *Cell* (1981) pp. 729-736, vol. 25.
Bethke, B., et al., "Segmental genomic replacement by Cre-mediated recombination: genotoxic stress activation of the p53 promoter in single-copy transformants", *Nucleic Acids Res.* (1997) pp. 2828-2834, vol. 25.
Buchholz, F., et al., "Alteration of Cre recombinase site specificity by substrate-linked protein evolution", *Biotech Nat.* (2001) pp. 1047-1052, vol. 19.
Dorgai, L., et al., "Identifying Determinants of Recombination Specificity: Construction and Characterization of Mutant Bacteriophage Integrases", *J. Mol. Biol.* (1995) pp. 178-188, vol. 252.

Eliason, J.L., et al., "Characterization of the Binding Sites of *c*1 Repressor of Bacteriophage P1", *J. Mol. Biol.* (1987) pp. 281-293, vol. 198.
Eustice, D.C., et al., "A Sensitive Method for the Detection of β-Galactosidase in Transfected Mammalian Cells", *BioTechniques* (1991) pp. 739-743, vol. 11.
Gabrielian, A., et al., "Correlation of intrinsic DNA curvature with DNA property periodicity", *FEBS Lett.* (1996) pp. 65-68, vol. 393.
Gagneten, S., et al., "Brief expression of a GFP*cre* fusion gene in embryonic stem cells allows rapid retrieval of site-specific genomic deletions", *Nucleic Acids Res.* (1997) pp. 3326-3331, vol. 25.
Guo, F., et al., "Structure of Cre recombinase complexed with DNA in a site-specific recombination synapse", *Nature* (1997) pp. 40-46, vol. 389.
Guzman, L.-M., et al., "Tight Regulation, Modulation, and High-Level Expression by Vectors Containing the Arabinose pBAD Promoter", *J. Bacteriol.* (1995) pp. 4121-4130, vol. 177.
Hartung, M., et al., "Cre Mutants with Altered DNA Binding Properties", *J. Biol. Chem.*(1998) pp. 22884-22891, vol. 273.
Heinrich, J., et al., "The tripartite immunity system of phages P1 and P7", *FEMS Microbiol. Rev.* (1995) pp. 121-126, vol. 17.
Hoess, R.H., et al., "P1 site-specific recombination: Nucleotide sequence of the recombining sites", *Proc. Natl. Acad. Sci. USA* (1982) pp. 3398-3402, vol. 79.
Ikeda, H., et al., "P1-like Plasmid in *Escherichia coli* 15", *J. Mol. Biol.* (1970) pp. 457-470, vol. 50.
Kim, S., et al., "Characterization of Cre-*lox*P Interaction in the Major Groove: Hint for Structural Distortion of Mutant Cre and Possible Strategy for HIV-1 Therapy", *J. Cell. Biochem.* (2001) pp. 321-327, vol. 80.
Laufer, C.S., et al., "Enhancement of *Escherichia coli* Plasmid and Chromosomal Recombination by the Ref Function of Bacteriophage P1", *Genetics* (1989) pp. 465-476, vol. 123.
Le, Y., et al., "GFP*cre* Fusion Vectors with Enhanced Expression", *Anal. Biochem.*(1999) pp. 334-336, vol. 270.
Lee, L. et al., "Sequence of the *lox*P Site Determines the Order of Strand Exchange by the Cre Recombinase", *J. Mol. Biol.* (2003) pp. 397-412, vol. 326.
Lennox, E.S., "Transduction of Linked Genetic Characters of the Host by Bacteriophage P1", *Virology* (1955) pp. 190-206, vol. 1.
Lu, S.D., et al., "Stimulation of IS*1* Excision by Bacteriophage P1 *ref*Function", *J. Bacteriol.* (1989) pp. 3427-3432, vol. 171.
Meyer, J., et al., "Sequence Relations among the IncY Plasmid p15B, P1, and P7 Prophages", *Plasmid* (1986) pp. 81-89, vol. 16.
Mise, K., et al., "New Generalized Transducing Bacteriophage in *Echerichia coli*", *J. Virol.* (1970) pp. 253-255, vol. 6.
Osborne, F.A., et al., "The c1 genes of P1 and P7", *Nucleic Acids Res.* (1989) pp. 7671-7680, vol. 17.
Petyuk, V., et al., "Functional Mapping of Cre Recombinase by Pentapeptide Insertional Mutagenesis", *J. Biol. Chem.* (2004), pp. 37040-37048, vol. 279.

(Continued)

*Primary Examiner*—Rebecca Prouty
(74) *Attorney, Agent, or Firm*—Bryan Cave LLP

(57) ABSTRACT

The invention provides a Dre/rox recombinase system. In particular, the invention provides Dre polypeptides that can catalyze site-specific recombination at rox sites but not at lox sites. The Dre/rox system can be utilized in a number of genetic manipulations either alone or in combination with other recombinase systems.

8 Claims, 8 Drawing Sheets
(4 of 8 Drawing Sheet(s) Filed in Color)

OTHER PUBLICATIONS

Rüfer, A.W., et al., "Non-contact positions impose site selectivity on Cre recombinase", *Nucleic Acids Res*.(2002) pp. 2764-2771, vol. 30.

Santoro, S.W., et al., "Directed evolution of the site specificity of Cre recombinase", *Proc. Natl. Acad. Sci. USA* (2002) pp. 4185-4190, vol. 99.

Sauer, B., "Manipulation of Transgenes by Site-Specific Recombination: Use of the Cre Recombinase", *Meth. Enzymol.* (1993) pp. 890-900, vol. 225.

Sauer, B., "Site-specific recombination: developments and applications", *Curr. Opin. Biotech.* (1994) pp. 521-527, vol. 5.

Sauer, B., et al., "Site-specific insertion of DNA into a pseudorabies virus vector",. *Proc. Natl. Acad. Sci. USA* (1987) pp. 9108-9112, vol. 84.

Sauer, B., et al., "Site-specific DNA recombination in mammalian cells by the Cre recombinase of bacteriophage P1", *Proc. Natl. Acad. Sci. USA* (1988) pp. 5166-5170, vol. 85.

Sauer, B., "Functional Expression of the *cre-lox* Site Specific Recombination System in the Yeast *Saccharomyces cerevisiae*", *Mol. Cell. Biol.* (1987) pp. 2087-2096, vol. 7.

Scott, J.R., "Genetic Studies on Bacteriophage P1", *Virology* (1968) pp. 564-574, vol. 36.

Smith, H.W., "Ampicillin Resistance in *Escherichia coli* by Phage Infection", *Nat. New Biol.* (1972) pp. 205-206, vol. 238.

Skorupski, K., et al., "Purification and DNA-Binding Activity of the PacA Subunit of the Bacteriophage P1 Pacase Enzyme", *J. Mol. Biol.* (1994) pp. 258-267, vol. 243.

Skorupski, K., et al., "Faithful Cleavage of the P1 Packaging Site (*pac*) Requires Two Phage Proteins, PacA and PacB, and Two *Escherichia coli* Proteins, IHF and HU", *J. Mol. Biol.* (1994) pp. 268-282, vol. 243.

Sternberg, N., et al., "Bacteriophage P1 *cre* Gene and its Regulatory Region: Evidence for Multiple Promoters and for Regulation by DNA Methylation", *J. Mol. Biol.* (1986) pp. 197-212, vol. 187.

Sternberg, N., et al., "Recognition and Cleavage of the Bacteriophage P1 Packaging Site (*pac*). II. Functional Limits of *pac* and Location of *pac* Cleavage Termini", *J. Mol. Biol.* (1987) pp. 469-479, vol. 194.

Sternberg, N., "Bacteriophage P1 cloning system for the isolation, amplification, and recovery of DNA fragments as large as 100 kilobase pairs", *Proc. Natl. Acad. Sci. USA* (1990) pp. 103-107, vol. 87.

Sternberg, N.L., "Bacteriophage-Mediated Generalized Transduction in *Escherichia coli* and *Salmonella typhimurium*", *Methods Enzymol.* (1991) pp. 18-43, vol. 204.

Swalla, B.M., et al., "Conservation of structure and function among tyrosine recombinases: homology-based modeling of the lambda integrase core-binding domain", *Nucleic Acids Res.* (2003) pp. 805-818, vol. 31.

Van Duyne, G.D., "A Structural View of Tyrosine Recombinase Site-Specific Recombination", (Craig, N. L., Craigie, R., Gellert, M. and Lambowitz, A. M. eds.), *Mobile DNA II* (2002) pp. 93-117/ASM Press, Washington, D.C.

Wall, J.D., et, al., "Phage P1 Mutants with Altered Transducing Abilities for *Escherichia coli*", *Virology* (1974) pp. 532-544, vol. 59.

Wandersman, C. et al., "Bipartite Control of Immunity Conferred by the Related Heteroimmune Plasmid Prophages, P1 and P7 (formerly φAmp)", *Virology* (1977) pp. 386-400, vol. 77.

Wierzbicki, A., et al., "A Mutational Analysis of the Bacteriophage P1 Recombinase Cre", *J. Mol. Biol.* (1987) pp. 785-794, vol. 195.

Yagil, E., et al., "Identifying Determinants of Recombination Specificity: Construction and Characterization of Chimeric Bacteriophage Integrases", *J. Mol. Biol.* (1995) pp. 163-177, vol. 252.

Yoshida, Y., et al., "Characterization of Generalized Transducing Phage φw39 Heteroimmune to Phage P1 in *Escherichia coli*W39", *Microbiol. Immunol.* (1984) pp. 415-426, vol. 28.

rox: 5' TAACTTTAAATAATGCCAATTATTTAAAGTTA (SEQ. ID NO. 5)
     3' ATTGAAATTTATTACGGTTAATAAATTTCAAT (SEQ. ID NO. 6)

lox: 5' ATAACTTCGTATAATGTATGCTATACGAAGTTAT (SEQ. ID NO. 7)
     3' TATTGAAGCATATTACATACGATATGCTTCAATA (SEQ. ID NO. 8)

```
                        SEQUENCE LISTING

<160> NUMBER OF SEQ ID NOS: 20

<210> SEQ ID NO 1
<211> LENGTH: 342
<212> TYPE: PRT
<213> ORGANISM: Enterobacteria phage D6

<400> SEQUENCE: 1

Met Ser Glu Leu Ile Ile Ser Gly Ser Ser Gly Gly Phe Leu Arg Asn
1               5                   10                  15

Ile Gly Lys Glu Tyr Gln Glu Ala Ala Glu Asn Phe Met Arg Phe Met
            20                  25                  30

Asn Asp Gln Gly Ala Tyr Ala Pro Asn Thr Leu Arg Asp Leu Arg Leu
        35                  40                  45

Val Phe His Ser Trp Ala Arg Trp Cys His Ala Arg Gln Leu Ala Trp
    50                  55                  60

Phe Pro Ile Ser Pro Glu Met Ala Arg Glu Tyr Phe Leu Gln Leu His
65                  70                  75                  80

Asp Ala Asp Leu Ala Ser Thr Thr Ile Asp Lys His Tyr Ala Met Leu
                85                  90                  95

Asn Met Leu Leu Ser His Cys Gly Leu Pro Pro Leu Ser Asp Asp Lys
            100                 105                 110

Ser Val Ser Leu Ala Met Arg Arg Ile Arg Arg Glu Ala Ala Thr Glu
        115                 120                 125

Lys Gly Glu Arg Thr Gly Gln Ala Ile Pro Leu Arg Trp Asp Asp Leu
    130                 135                 140

Lys Leu Leu Asp Val Leu Leu Ser Arg Ser Glu Arg Leu Val Asp Leu
145                 150                 155                 160
```

Arg Asn Arg Ala Phe Leu Phe Val Ala Tyr Asn Thr Leu Met Arg Met
              165                 170                 175

Ser Glu Ile Ser Arg Ile Arg Val Gly Asp Leu Asp Gln Thr Gly Asp
            180                 185                 190

Thr Val Thr Leu His Ile Ser His Thr Lys Thr Ile Thr Thr Ala Ala
        195                 200                 205

Gly Leu Asp Lys Val Leu Ser Arg Arg Thr Thr Ala Val Leu Asn Asp
    210                 215                 220

Trp Leu Asp Val Ser Gly Leu Arg Glu His Pro Asp Ala Val Leu Phe
225                 230                 235                 240

Pro Pro Ile His Arg Ser Asn Lys Ala Arg Ile Thr Thr Thr Pro Leu
                245                 250                 255

Thr Ala Pro Ala Met Glu Lys Ile Phe Ser Asp Ala Trp Val Leu Leu
            260                 265                 270

Asn Lys Arg Asp Ala Thr Pro Asn Lys Gly Arg Tyr Arg Thr Trp Thr
        275                 280                 285

Gly His Ser Ala Arg Val Gly Ala Ala Ile Asp Met Ala Glu Lys Gln
    290                 295                 300

Val Ser Met Val Glu Ile Met Gln Glu Gly Thr Trp Lys Lys Pro Glu
305                 310                 315                 320

Thr Leu Met Arg Tyr Leu Arg Arg Gly Gly Val Ser Val Gly Ala Asn
                325                 330                 335

Ser Arg Leu Met Asp Ser
            340

<210> SEQ ID NO 2
<211> LENGTH: 343
<212> TYPE: PRT
<213> ORGANISM: Enterobacteria phage thetaw39

<400> SEQUENCE: 2

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

```
Met Leu Ile His Ile Gly Arg Thr Lys Thr Leu Val Ser Ala Ala Gly
            195                 200                 205

Val Glu Lys Ala Leu Ser Leu Gly Val Thr Lys Leu Val Glu Arg Trp
        210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
            260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340

<210> SEQ ID NO 3
<211> LENGTH: 343
<212> TYPE: PRT
<213> ORGANISM: Enterobacteria phage P7

<400> SEQUENCE: 3

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ser Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220
```

-continued

```
Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
            260                 265                 270

Tyr Gly Ala Lys Asp Asp Ser Asp Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340
```

<210> SEQ ID NO 4
<211> LENGTH: 343
<212> TYPE: PRT
<213> ORGANISM: Enterobacteria phage p15B

<400> SEQUENCE: 4

```
Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
                20                  25                  30

Asp Arg Gln Ala Phe Ser Glu His Thr Trp Lys Met Leu Leu Ser Val
            35                  40                  45

Cys Arg Ser Trp Ala Ala Trp Cys Lys Leu Asn Asn Arg Lys Trp Phe
        50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Leu Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ser Pro Ser Pro Thr Ser Gln Leu
                245                 250                 255
```

-continued

| Ser | Thr | Arg | Ala | Leu | Glu | Gly | Ile | Phe | Glu | Ala | Thr | His | Arg | Leu | Ile |
|-----|-----|-----|-----|-----|-----|-----|-----|-----|-----|-----|-----|-----|-----|-----|-----|
|     |     |     |     | 260 |     |     |     |     | 265 |     |     |     |     | 270 |     |

| Tyr | Gly | Ala | Lys | Asp | Asp | Ser | Gly | Gln | Arg | Tyr | Leu | Ala | Trp | Ser | Gly |
|-----|-----|-----|-----|-----|-----|-----|-----|-----|-----|-----|-----|-----|-----|-----|-----|
|     |     |     | 275 |     |     |     |     | 280 |     |     |     |     | 285 |     |     |

| His | Ser | Ala | Arg | Val | Gly | Ala | Ala | Arg | Asp | Met | Ala | Arg | Ala | Gly | Val |
|-----|-----|-----|-----|-----|-----|-----|-----|-----|-----|-----|-----|-----|-----|-----|-----|
|     |     | 290 |     |     |     |     | 295 |     |     |     |     | 300 |     |     |     |

| Ser | Ile | Pro | Glu | Ile | Met | Gln | Ala | Gly | Gly | Trp | Thr | Asn | Val | Asn | Ile |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |

| Val | Met | Asn | Tyr | Ile | Arg | Asn | Leu | Asp | Ser | Glu | Thr | Gly | Ala | Met | Val |
|-----|-----|-----|-----|-----|-----|-----|-----|-----|-----|-----|-----|-----|-----|-----|-----|
|     |     |     |     | 325 |     |     |     |     | 330 |     |     |     |     | 335 |     |

| Arg | Leu | Leu | Glu | Asp | Gly | Asp |
|-----|-----|-----|-----|-----|-----|-----|
|     |     |     | 340 |     |     |     |

<210> SEQ ID NO 5
<211> LENGTH: 32
<212> TYPE: DNA
<213> ORGANISM: Enterobacteria phage D6

<400> SEQUENCE: 5
taactttaaa taatgccaat tatttaaagt ta                           32

<210> SEQ ID NO 6
<211> LENGTH: 32
<212> TYPE: DNA
<213> ORGANISM: Enterobacteria phage D6

<400> SEQUENCE: 6
attgaaattt attacggtta ataaatttca at                           32

<210> SEQ ID NO 7
<211> LENGTH: 34
<212> TYPE: DNA
<213> ORGANISM: Enterobacteria phage P1

<400> SEQUENCE: 7
ataacttcgt ataatgtatg ctatacgaag ttat                         34

<210> SEQ ID NO 8
<211> LENGTH: 34
<212> TYPE: DNA
<213> ORGANISM: Enterobacteria phage P1

<400> SEQUENCE: 8
tattgaagca tattacatac gatatgcttc aata                         34

<210> SEQ ID NO 9
<211> LENGTH: 38
<212> TYPE: DNA
<213> ORGANISM: Enterobacteria phage P1

<400> SEQUENCE: 9
ctagataact ttaaataatt ggcattattt aaagttag                     38

<210> SEQ ID NO 10
<211> LENGTH: 38
<212> TYPE: DNA
<213> ORGANISM: Enterobacteria phage P1

<400> SEQUENCE: 10
gatcctaact ttaaataatg ccaattattt aaagttat                     38

```
<210> SEQ ID NO 11
<211> LENGTH: 39
<212> TYPE: DNA
<213> ORGANISM: Enterobacteria phage P1

<400> SEQUENCE: 11
ctagctataa cttcgtataa tgtatgctat acgaagttg                              39

<210> SEQ ID NO 12
<211> LENGTH: 39
<212> TYPE: DNA
<213> ORGANISM: Enterobacteria phage P1

<400> SEQUENCE: 12
tcgacaactt cgtatagcat acattatacg aagttatag                              39

<210> SEQ ID NO 13
<211> LENGTH: 47
<212> TYPE: DNA
<213> ORGANISM: Enterobacteria phage P1

<400> SEQUENCE: 13
agatggtacc aggaggatat caatatgagt gaattaatta tctctgg                    47

<210> SEQ ID NO 14
<211> LENGTH: 36
<212> TYPE: DNA
<213> ORGANISM: Enterobacteria phage P1

<400> SEQUENCE: 14
ctttagtcta gattcattat gaatccatca agcggc                                 36

<210> SEQ ID NO 15
<211> LENGTH: 27
<212> TYPE: DNA
<213> ORGANISM: Enterobacteria phage P1

<400> SEQUENCE: 15
gcttggcact tgatgtaatt ctccttg                                           27

<210> SEQ ID NO 16
<211> LENGTH: 21
<212> TYPE: DNA
<213> ORGANISM: Enterobacteria phage P1

<400> SEQUENCE: 16
ggtcagcttg ccgtaggtgg c                                                 21

<210> SEQ ID NO 17
<211> LENGTH: 13
<212> TYPE: DNA
<213> ORGANISM: Enterobacteria phage P1

<400> SEQUENCE: 17
aaacaaagag tta                                                          13

<210> SEQ ID NO 18
<211> LENGTH: 13
<212> TYPE: DNA
<213> ORGANISM: Enterobacteria phage P1

<400> SEQUENCE: 18
aaacagagag tta                                                          13
```

<210> SEQ ID NO 19
<211> LENGTH: 70
<212> TYPE: DNA
<213> ORGANISM: Enterobacteria phage P1

<400> SEQUENCE: 19
tgatggatta aaaaaaatcg gcattttata actttaaata attggcatta tttaaagtta    60
ggctataatc                                                            70

<210> SEQ ID NO 20
<211> LENGTH: 343
<212> TYPE: PRT
<213> ORGANISM: Enterobacteria phage P1

<400> SEQUENCE: 20

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
            260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Pro Glu Ile Met Gln Ala Gly Gly Trp Thr Asn Val Asn Ile
305                 310                 315                 320

```
                                    -continued
Val Met Asn Tyr Ile Arg Asn Leu Asp Ser Glu Thr Gly Ala Met Val
                325                 330                 335

Arg Leu Leu Glu Asp Gly Asp
            340
```

DRE RECOMBINASE AND RECOMBINASE SYSTEMS EMPLOYING DRE RECOMBINASE

CROSS-REFERENCE TO RELATED APPLICATION

This application claims priority from Provisional Application Ser. No. 60/623,701 filed on Oct. 29, 2004, which is hereby incorporated by reference in its entirety.

FIELD OF THE INVENTION

The current invention generally relates to Dre recombinase and recombinase systems employing Dre recombinase. In particular, the present invention relates to a Dre recombinase that can catalyze site specific recombination at a rox site. The Dre/rox system can be utilized in a number of genetic manipulations either alone or in combination with other recombinase systems.

BACKGROUND OF THE INVENTION

The use of site-specific DNA recombinases has expanded the spectrum of genetic manipulations that can be carried out in both prokaryotic and eukaryotic organisms. While various site-specific DNA recombinases, such as the yeast-derived Flp/frt, are becoming increasingly popular, the Cre/loxP system is currently the most widely used system. Because of its simplicity and versatility, Cre has found widespread use in conditional mutagenesis and gene expression, gene replacement and deletion, and chromosomal engineering experiments.

Cre is a site-specific DNA recombinase derived from the P1 bacteriophage and is a member of the lambda integrase or tyrosine family of site-specific recombinases (1). Members of this family catalyze DNA recombination by a common catalytic mechanism and recognize target recombination sites with similar structural features. In the case of the Cre protein, it recognizes 34 base pair sequences known as loxP sites. The loxP sequence is composed of an asymmetric eight base pair spacer region flanked by 13 base pair inverted repeats. Cre recombines the 34 base pair loxP DNA sequence by binding to the 13 base pair inverted repeats and catalyzing strand cleavage and religation within the spacer region. The staggered DNA cuts made by Cre in the spacer region are separated by 6 base pairs to give an overlap region that acts as a homology sensor to ensure that only recombination sites having the same overlap region recombine.

The P1 genome, the sequencing of which has recently been completed in its entirety (12), is relatively large for a temperate DNA bacteriophage: 95 kb. P1 is unusual among temperate bacteriophages in that it maintains itself as an extrachromosomal unit copy plasmid in the lysogenic state. Cre is expressed in P1 lysogens and its site-specific DNA recombination activity contributes to the stable maintenance of the P1 prophage during lysogeny. Cre resolves P1 dimers that arise by homologous recombination after DNA replication, thus helping to ensure segregation of a P1 monomer to each daughter cell at cell division (13).

The P1 Cre gene and its 34 bp recombination target site loxP lie in a relatively short interval of P1 DNA that includes two other phage functions with unusual features. To the left of Cre is the immC immunity region of P1 that encodes the C1 repressor and several other immunity proteins that modify its action. ImmC, in turn, lies just to the right of the two genes for the P1 pacase or terminase and the pac site at which P1 DNA packaging begins. DNA packaging in P1 is unusual because protein recognition of the P1 DNA packaging site is regulated by DNA adenine methylation (dam). Although immunity in P1 is orchestrated in a complex manner and includes several different immunity regions (16), including antirepressor components, the C1 protein is unusual compared to other phage repressors because it recognizes an asymmetric DNA binding site (17). To the left of the P1 Cre gene is c8, another immunity gene, followed by ref, a gene involved in the homologous recombination of short DNA repeats (18,19).

Several P1-related phages also maintain themselves as an extrachromosomal plasmid in the lysogenic state, but comparable recombinase function in these P-1 related phages has yet to be elucidated. In particular, Cre homologues that perform site specific recombination at sites distinguishable from the lox site have not been previously characterized.

SUMMARY OF THE INVENTION

Among the several aspects of the invention, therefore, is the provision of a Dre recombinase that catalyzes site specific recombination at a rox site instead of at a lox site. Advantageously, because of this difference in substrate specificity, the Dre recombinase of the present invention provides an additional tool that may be utilized either alone or in combination with other Cre/lox systems for conditional mutagenesis and gene expression, gene replacement and deletion, and chromosome engineering.

One aspect of the invention encompasses a purified Dre polypeptide that can catalyze site specific recombination at a rox site. In one embodiment, the Dre polypeptide has an amino acid sequence comprising SEQ ID NO. 1. In still another alternative of this embodiment, the Dre polypeptide has an amino acid sequence such that it specifically binds to an antibody that binds specifically to a polypeptide having the amino acid sequence of SEQ ID NO. 1.

Yet another aspect of the invention provides isolated nucleotide sequences that encode Dre mutant polypeptides that can catalyze site specific recombination at a rox site. In one alternative of this embodiment, the isolated nucleotide sequence comprises a sequence that encodes a polypeptide having the amino acid sequence of SEQ ID NO. 1, or of a fragment SEQ ID NO. 1 that is at least 15 amino acid residues in length. In another alternative of this embodiment, the isolated nucleotide sequence comprises a sequence that hybridizes under stringent conditions to a hybridization probe the nucleotide sequence of which encodes a polypeptide having the amino acid sequence of SEQ ID NO. 1.

A further aspect of the invention provides purified antibodies that are specific for a Dre polypeptide of the invention. In one embodiment, the purified antibody binds specifically to a polypeptide having the amino acid sequence of SEQ ID NO. 1. The purified antibodies may be either monoclonal or polyclonal antibodies and may be used to purify Dre polypeptides of the present invention.

An additional aspect of the invention encompasses an isolated rox nucleotide sequence having the following structure:

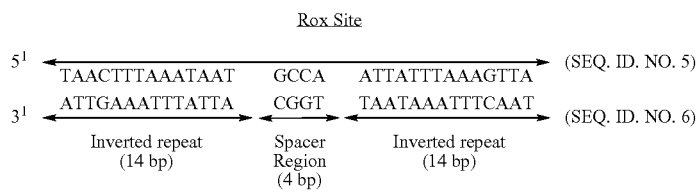

Yet another aspect of the invention encompasses a Dre/rox system. The system typically comprises a purified Dre polypeptide that can catalyze site specific recombination at a rox site.

A further aspect of the invention provides a method for producing site-specific recombination of nucleotide sequence having a target DNA segment. The method involves introducing a first rox site and a second rox site into the nucleotide sequence such that the rox sites flank the target DNA segment. The rox sites are then contacted with a Dre polypeptide that can catalyze site specific recombination at a rox site. When the Dre polypeptide is contacted with the rox sites, site specific recombination of the nucleotide sequence occurs.

An additional aspect of the invention encompasses a kit for producing site-specific recombination of nucleotide sequence. Typically, the kit will comprise a purified Dre polypeptide that can catalyze site specific recombination at a rox site; an isolated rox nucleotide sequence; and instructions for producing site specific recombination.

A further aspect of the invention encompasses cells and nucleic acid sequences having the Dre polypeptides and rox sites of the invention.

Other objects and features of the invention will be in part apparent and in part pointed out hereinafter.

BRIEF DESCRIPTION OF THE FIGURES

The application contains at least one drawing executed in color. Copies of this patent and/or application publication with color drawing(s) will be provided by the Office upon request and payment of the necessary fee.

DETAILED DESCRIPTION OF THE PREFFERED EMBODIMENTS

Figure 1:
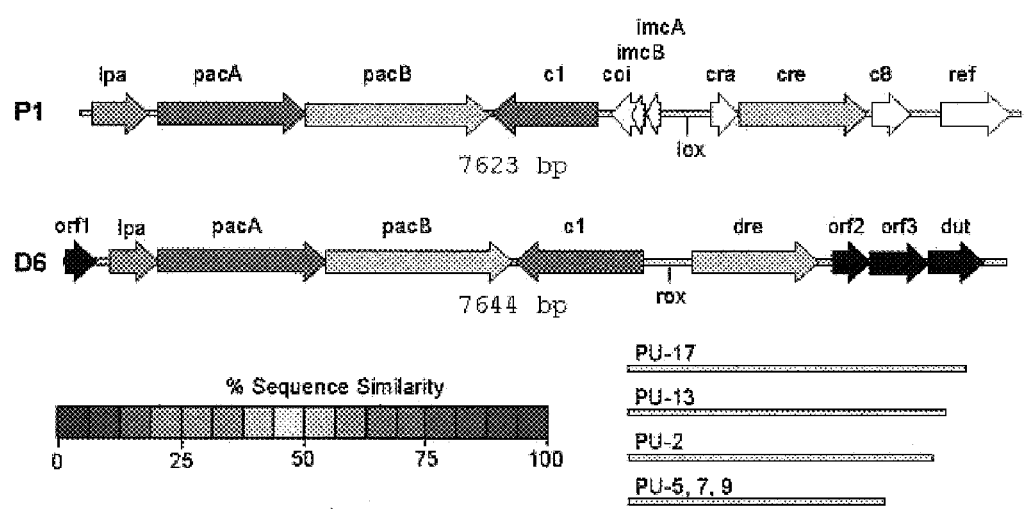
FIG. 1 depicts a schematic comparing the pac-c1 regions of P1 and D6. Shown is a 7623 bp region of P1 that includes the region from lpa (gene 10) to ref. Also shown is the corresponding 7644 bp region from D6. The degree of similarity between individual genes of P1 and D6 is indicated according to the color scale shown. P1 genes in white have no D6 equivalent in this region, D6 genes in black have no P1 equivalent. Below and aligned with the D6 map is diagrammed the DNA insert of several PU (pickup) clones obtained by site-specific recombination.
Figure 2:
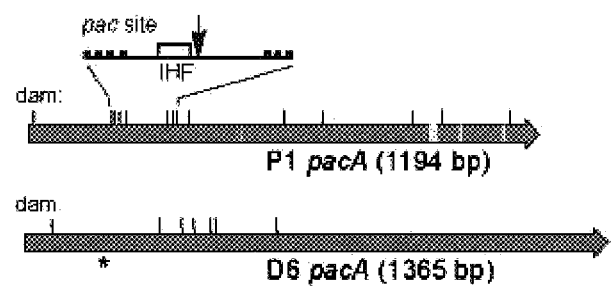
FIG. 2 depicts a schematic comparing the P1 and D6 pacA genes. Dam methylation sites for both genes are shown as vertical lines above the gene. A blowup of the 162 bp P1 pac site that includes two clusters of dam sites is shown above the P1 pacA gene, with dam sites represented as black boxes, the IHF binding site as a white rectangle and the region of cleavage as a vertical arrow. An asterisk at nucleotide position 182 of D6 pacA marks the maximum of a curvature-propensity plot calculated with DNase I-based trinucleotide parameters (37).

The present invention provides a Dre recombinase and several Cre homologues identified from P1-related phages that can be employed in novel recombinase systems. Dre recombinase recognizes a rox site instead of a lox site. Because of this difference in substrate specificity, advantageously, the Dre/rox recombinase system of the present invention provides an additional tool that may be utilized either alone or in combination with other Cre/lox systems for conditional mutagenesis and gene expression, gene replacement and deletion, and chromosome engineering.

Dre Recombinase

One aspect of the invention provides a Dre recombinase polypeptide having SEQ ID NO. 1. Dre catalyzes site specific recombination at a rox site, the nucleotide sequence of which is described below. In particular, Dre and wild-type Cre are heterospecific in that Cre does not catalyze site specific recombination at a rox site and Dre does not catalyze site specific recombination at a lox site. In one alternative of this embodiment, a polypeptide is provided that has an amino acid sequence such that it specifically binds to an antibody that binds specifically to the Dre polypeptide having SEQ ID NO. 1. Typically, suitable polypeptides in this embodiment will have an amino acid sequence that is at least 50% identical to SEQ ID NO.1, and more typically, the polypeptide will have an amino acid sequence that is at least 75% identical to SEQ ID NO.1. Exemplary polypeptides, however, will have an amino acid sequence that is at least 90%, more preferably 95%, and even more preferably, 99% identical to SEQ ID NO. 1. In a further alternative of this embodiment, the polypeptide will have an amino acid sequence that comprises SEQ. ID. NO.1 with 1 to 50 conservative amino acid substitutions. In an exemplary alternative of this embodiment, the polypeptide will have an amino acid sequence that comprises SEQ ID NO. 1 with 1 to 15, and more typically, from 1 to 10 conservative amino acid substitutions. In each of these embodiments, typically the polypeptide can catalyze site specific recombination or excision at a rox site, but not a lox site.

Cre Homologues

A further aspect of the present invention provides, as detailed in the examples, Cre homologue polypeptides identified from P1-related phages that can catalyze site specific recombination at a lox site. In a one embodiment, the Cre homologue is a polypeptide having SEQ ID NO. 2. In one alternative of this embodiment, a polypeptide is provided that has an amino acid sequence such that it specifically binds to an antibody that binds specifically to a polypeptide having SEQ ID NO. 2. Typically, a polypeptide in this embodiment will have an amino acid sequence that is at least 50% identical to SEQ ID NO. 2, and more typically, the polypeptide will have an amino acid sequence that is at least 75% identical to SEQ ID NO. 2. Exemplary polypeptides, however, will have an amino acid sequence that is at least 90%, more preferably 95%, and even more preferably, 99% identical to SEQ ID NO. 2. In a further alternative of this embodiment, the polypeptide will have an amino acid sequence that comprises SEQ. ID. NO. 2 with 1 to 50 conservative amino acid substitutions. In an exemplary alternative of this embodiment, the polypeptide will have an amino acid sequence that comprises SEQ ID NO. 2 with 1 to 15, and more typically, from 1 to 10 conservative amino acid substitutions. In each of these embodiments, typically the polypeptide can catalyze site specific recombination or excision at a lox site.

In still another alternative embodiment, the Cre homologue is a polypeptide having SEQ ID No. 3. In one alternative of this embodiment, the polypeptide has an amino acid sequence such that it specifically binds to an antibody that binds specifically to a polypeptide having SEQ ID NO. 3. Preferably, polypeptides in this embodiment will have an amino acid sequence that is at least 50% identical to SEQ ID NO. 3, and more typically, the polypeptide will have an amino acid sequence that is at least 75% identical to SEQ ID NO. 3. Exemplary polypeptides, however, will have an amino acid sequence that is at least 90%, more preferably 95%, and even more preferably, 99% identical to SEQ ID NO. 3. In a further alternative of this embodiment, the polypeptide will have an amino acid sequence that comprises SEQ. ID. NO. 3 with 1 to 50 conservative amino acid substitutions. In an exemplary alternative of this embodiment, the polypeptide will have an amino acid sequence that comprises SEQ ID NO. 3 with 1 to 15, and more typically, from 1 to 10 conservative amino acid substitutions. In each of these embodiments, typically the polypeptide can catalyze site specific recombination or excision at a lox site.

In yet a further alternative embodiment, the Cre homologue is a polypeptide having SEQ ID No. 4. In one aspect of the invention, the polypeptide has an amino acid sequence such that it specifically binds to an antibody that binds specifically to a polypeptide having SEQ ID NO. 4. Typically, polypeptides in this embodiment will have an amino acid sequence that is at least 50% identical to SEQ ID NO.4, and more typically, the polypeptide will have an amino acid sequence that is at least 75% identical to SEQ ID NO. 4. Exemplary polypeptides, however, will have an amino acid sequence that is at least 90%, more preferably 95%, and even more preferably, 99% identical to SEQ ID NO. 4. In a further alternative of this embodiment, the polypeptide will have an amino acid sequence that comprises SEQ. ID. NO. 4 with 1 to 50 conservative amino acid substitutions. In an exemplary alternative of this embodiment, the polypeptide will have an amino acid sequence that comprises SEQ ID NO. 4 with 1 to 15, and more typically, from 1 to 10 conservative amino acid substitutions. In each of these embodiments, typically the polypeptide can catalyze site specific recombination or excision at a lox.

Because of the somewhat ubiquitous nature of the Dre polypeptide or Cre homologues of the invention, it will be appreciated by those skilled in the art that additional suitable Dre polypeptides or Cre homologue polypeptides exist other than the ones specifically detailed herein. It will also be appreciated that additional polypeptides may be present in a species in addition to the polypeptides detailed herein. The invention contemplates the use of all suitable Dre polypeptides or Cre homologue polypeptides having the structure and function as described herein.

In certain aspects, accordingly, a polypeptide that is a homolog, ortholog, or degenerative variant of a Dre polypeptide or Cre homologue polypeptide is also suitable for use in the present invention. Typically, the subject polypeptides include fragments that share substantial sequence similarity, binding specificity and function with any of the polypeptides detailed above, including any of the polypeptides having SEQ ID Nos. 1, 2, 3, or 4.

A number of methods may be employed to determine whether a particular homolog or degenerative variant possesses substantially similar biological activity relative to a Dre polypeptide or Cre homologue of the invention. In particular, the subject polypeptide, if suitable for use in the invention, will be able to catalyze site specific recombination or excision at a lox site or a rox site, depending upon the particular embodiment. In order to determine whether a particular polypeptide can function in this manner, either the in vitro or in vivo recombination assays detailed in the examples may be followed.

In determining whether a polypeptide is substantially homologous or shares a certain percentage of sequence identity with a polypeptide of the invention, sequence similarity may be determined by conventional algorithms, which typically allow introduction of a small number of gaps in order to achieve the best fit. In particular, "percent homology" of two polypeptides or two nucleic acid sequences is determined using the algorithm of Karlin and Altschul (Proc. Natl. Acad. Sci. USA 87:2264-2268, 1993). Such an algorithm is incorporated into the NBLAST and XBLAST programs of Altschul et al. (J. Mol. Biol. 215:403-410, 1990). BLAST nucleotide searches may be performed with the NBLAST program to obtain nucleotide sequences homologous to a nucleic acid molecule of the invention. Equally, BLAST protein searches may be performed with the XBLAST program to obtain amino acid sequences that are homologous to a polypeptide of the invention. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g., XBLAST and NBLAST) are employed. See http://www.ncbi.nlm.nih.gov for more details.

Dre polypeptides or Cre homologue polypeptides suitable for use in the invention are typically isolated or pure. An "isolated" polypeptide is unaccompanied by at least some of the material with which it is associated in its natural state, preferably constituting at least about 0.5%, and more preferably, at least about 5% by weight of the total polypeptide in a given sample. A pure polypeptide constitutes at least about 90%, preferably, 95% and even more preferably, at least about 99% by weight of the total polypeptide in a given sample. In certain embodiments a pure polypeptide is preferred because all unwanted material, such as cellular debris, is removed. In other embodiments, polypeptides that are not pure may be utilized. A skilled artisan can readily select a polypeptide having the desired degree of purity for any particular application.

The polypeptides may be synthesized, produced by recombinant technology, or purified from cells. In one embodiment, the polypeptide of the present invention may be obtained by direct synthesis. In addition to direct synthesis, the subject polypeptides can also be expressed in cell and cell-free systems (e.g. Jermutus L, et al., Curr Opin Biotechnol. October 1998; 9(5):534-48) from encoding polynucleotides, such as described below or naturally-encoding polynucleotides isolated with degenerate oligonucleotide primers and probes generated from the subject polypeptide sequences ("GCG" software, Genetics Computer Group, Inc, Madison Wis.) or polynucleotides optimized for selected expression systems made by back-translating the subject polypeptides according to computer algorithms (e.g. Holler et al. (1993) Gene 136, 323-328; Martin et al. (1995) Gene 154, 150-166). In other embodiments, any of the molecular and biochemical methods known in the art are available for biochemical synthesis, molecular expression and purification of a Dre polypeptide or Cre homologue polypeptide, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, New York).

Dre and Cre Homologue Nucleotide Sequences

The present invention also encompasses the use of isolated nucleotide sequences that encode suitable Dre polypeptides or Cre homologue polypeptides. For example, the subject nucleotide sequences may be utilized as a means to produce a polypeptide having the structure and biological activity as detailed above.

The nucleotide sequence may be any of a number of such nucleotide sequences that encode a suitable Dre polypeptide or Cre homologue polypeptide, having the structure and function as described herein. In one embodiment, the isolated nucleotide is a sequence that encodes a polypeptide having an amino acid sequence selected from the group consisting of SEQ ID NO. 1, 2, 3, or 4 or of a fragment of any of SEQ ID NO. 1, 2, 3, or 4 that is at least 15 amino acid residues in length.

In still another embodiment, the isolated nucleotide sequence will encode a polypeptide that has an amino acid sequence that is at least 50% identical to the amino acid sequence of any of SEQ ID NO. 1, 2, 3, or 4. More typically, however, the isolated nucleotide sequence will encode a polypeptide that has an amino acid sequence that is at least 75% identical to the amino acid sequence of any of SEQ ID NO. 1, 2, 3, or 4 and even more typically, 90% identical to the amino acid sequence of any of SEQ ID NO. 1, 2, 3, or 4. In a particularly preferred embodiment, the nucleotide sequence will encode a polypeptide that has an amino acid sequence that is at least 95%, and even more preferably, 99% identical to the amino acid sequence of any of SEQ ID NO. 1, 2, 3, or 4. In each of these embodiments, the isolated nucleotide sequence will preferably encode a polypeptide that will be able to catalyze site specific recombination or excision at a lox or rox site, depending upon the embodiment.

The invention also encompasses the use of nucleotide sequences other than a sequence that encodes a polypeptide having an amino acid sequence selected from the group consisting of SEQ ID NO. 1, 2, 3, or 4. Typically, these nucleotide sequences will hybridize under stringent hybridization conditions (as defined herein) to all or a portion of the nucleotide sequences described above or their complement. The hybridizing portion of the hybridizing nucleic acids is usually at least 15 (e.g., 20, 25, 30, or 50) nucleotides in length. The hybridizing portion of the hybridizing nucleic acid is at least 80%, preferably, at least 90%, and is more preferably, at least 95% identical to the sequence of a portion or all of a nucleic acid sequence encoding a polypeptide suitable for use in the present invention, or its complement.

Hybridization of the oligionucleotide probe to a nucleic acid sample is typically performed under stringent conditions. Nucleic acid duplex or hybrid stability is expressed as the melting temperature or Tm, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g., SSC or SSPE). Then, assuming at 1% mismatching results in a 1° C. decrease in the Tm, the temperature of the final wash in the hybridization reaction is reduced accordingly. For example, if sequences have greater than 95% identity with the probe is sought, the final temperature is approximately decreased by 5° C. In practice, the change in Tm can be between 0.5 and 1.5° C. per 1% mismatch. Stringent conditions involve hybridizing at 68° C. in 5×SSC/5×Denhardt's solution/1.0% SDS, and washing in 0.2×SSC/0.1% SDS at room temperature. Moderately stringent conditions include washing in 3×SSC at 42° C. The parameters of salt concentration and temperature can be varied to achieve the optimal level of identity between the probe and the subject nucleotide sequence. Additional guidance regarding such conditions is readily available in the art, for example, by Sambrook et al., 1989, Molecular Cloning, A Laboratory Manual, Cold Spring Harbor Press, N.Y.; and Ausubel et al., (eds.), 1995, Current Protocols in Molecular Biology, (John Wiley & Sons, N.Y.) at Unit 2.10.

The various nucleic acid sequences mentioned above can be obtained using a variety of different techniques known in the art. The nucleotide sequences, as well as homologous sequences encoding a suitable polypeptide, can be isolated using standard techniques, or can be purchased or obtained from a depository. Once the nucleotide sequence is obtained, it can be amplified for use in a variety of applications, as further described below.

The invention also encompasses production of nucleotide sequences that encode suitable polypeptide homologs, derivatives, or fragments thereof, that may be made by any method known in the art, including by synthetic chemistry. After production, the synthetic sequence may be inserted into any of the many available expression vectors and cell systems using reagents well known in the art. Moreover, synthetic chemistry may be used to introduce additional mutations into a nucleotide sequence encoding a suitable polypeptide.

The nucleotide sequences of the present invention can be engineered using methods generally known in the art in order to alter a subject polypeptides-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

Vectors

In order to express a biologically active Dre polypeptide, the nucleotide sequences encoding such polypeptides may be inserted into an appropriate expression vector. Non limiting examples of suitable expression vector are described in the examples. An "appropriate vector" is typically a vector that contains the necessary elements for transcriptional and translational control of the inserted coding sequence in a suitable host. These elements generally will include regulatory sequences, such as enhancers, constitutive and inducible promoters, and 5' and 3' untranslated regions in the vector and polynucleotide sequences encoding a Dre polypeptide of the invention. Such elements may vary in their strength and specificity. Specific initiation signals may also be used to achieve more efficient translation of nucleotide sequences encoding Dre polypeptides. These signals, for example, include the ATG initiation codon and adjacent sequences (e.g. the Kozak sequence). In cases where nucleotide sequences encoding the subject polypeptide and its initiation codon and upstream regulatory sequences are inserted into the appropriate expression vector, no additional transcriptional or translational control signals may be needed. But in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used (See, e.g., Scharf, D. et al. (1994) Results Probl. Cell Differ. 20:125-162).

Depending upon the embodiment, either eukaryotic or prokaryotic vectors may be used. Suitable eukaryotic vectors that may be used include MSCV, Harvey murine sarcoma virus, pFastBac, pFastBac HT, pFastBac DUAL, pSFV, pTet-Splice, pEUK-C1, pPUR, pMAM, pMAMneo, pBI101, pBI121, pDR2, pCMVEBNA, YACneo, pSVK3, pSVL, pMSG, pCH110, pKK232-8, p3'SS, pBlueBacIII, pCDM8, pcDNA1, pZeoSV, pcDNA3, pREP4, pCEP4, and pEBVHis vectors. The MSCV or Harvey murine sarcoma virus is preferred. Suitable prokaryotic vectors that can be used in the present invention include pET, pET28, pcDNA3.1/V5-His-TOPO, pCS2+, pcDNA II, pSL301, pSE280, pSE380, pSE420, pTrcHis, pRSET, pGEMEX-1, pGEMEX-2, pTrc99A, pKK223-3, pGEX, pEZZ18, pRIT2T, pMC1871, pKK233-2, pKK38801, and pProEx-HT vectors.

Methods that are well known to those skilled in the art may be used to construct expression vectors containing sequences encoding the Dre polypeptide and appropriate transcriptional and translational control elements. These methods include, for example, in vitro recombinant DNA techniques, synthetic techniques, and in vivo genetic recombination. (See, e.g., Sambrook, J. et al. (1989) Molecular Cloning, A Laboratory Manual, Cold Spring Harbor Press, Plainview N.Y., ch. 4, 8, and 16-17; Ausubel, F. M. et al. (1995) Current Protocols in Molecular Biology, John Wiley & Sons, New York N.Y., ch. 9, 13, and 16).

It is also contemplated that a variety of expression vector/host systems may be utilized to contain and express nucleotide sequences encoding polypeptides of the invention. By way of non limiting example, these include microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus, CaMV, or tobacco mosaic virus, TMV) or with bacterial expression vectors (e.g., Ti or pBR322 plasmids); or animal cell systems. (See, e.g., Sambrook, supra; Ausubel, supra; Van Heeke, G. and S. M. Schuster (1989) J. Biol. Chem. 264:5503-5509; Engelhard, E. K. et al. (1994) Proc. Natl. Acad. Sci. USA 91:3224-3227; Sandig, V. et al. (1996) Hum. Gene Ther. 7:1937-1945; Takamatsu, N. (1987) EMBO J. 6:307-311; The McGraw Hill Yearbook of Science and Technology (1992) McGraw Hill, New York N.Y., pp. 191-196; Logan, J. and T. Shenk (1984) Proc. Natl. Acad. Sci. USA 81:3655-3659; and Harrington, J. J. et al. (1997) Nat. Genet. 15:345-355). In additional embodiments, expression vectors derived from retroviruses, adenoviruses, or herpes or vaccinia viruses, or from various bacterial plasmids, may be used for delivery of nucleotide sequences to the targeted organ, tissue, or cell population. (See, e.g., Di Nicola, M. et al. (1998) Cancer Gen. Ther. 5(6):350-356; Yu, M. et al. (1993) Proc. Natl. Acad. Sci. USA 90(13):6340-6344; Buller, R. M. et al. (1985) Nature 317 (6040):813-815; McGregor, D. P. et al. (1994) Mol. Immunol. 31(3):219-226; and Verma, L M. and N. Somia (1997) Nature 389:239-242).

In one aspect of the invention, accordingly, a bacterial expression system is employed. In bacterial systems, a number of cloning and expression vectors may be selected depending upon the use intended for nucleotide sequence. For example, routine cloning, subcloning, and propagation of nucleotide sequences can be achieved using a multifunctional E. coli vector such as PBLUESCRIPT (Stratagene, La Jolla Calif.) or PSPORT1 plasmid (Life Technologies). Ligation of nucleotide sequences encoding Dre polypeptides into the vector's multiple cloning sites disrupts the lacZ gene, advantageously allowing a calorimetric screening procedure for identification of transformed bacteria containing the subject recombinant molecule. When large quantities of polypeptide are needed, vectors that direct high level expression of Dre polypeptides may be used. For example, vectors containing the strong, inducible SP6 or T7 bacteriophage promoter may be used for this embodiment.

A further aspect of the invention encompasses the use of yeast expression systems. In this embodiment, a number of vectors containing constitutive or inducible promoters, such as alpha factor, alcohol oxidase, and PGH promoters, may be used in the yeast *Saccharomyces cerevisiae* or *Pichia pastoris*. In addition, such vectors advantageously direct either the secretion or intracellular retention of expressed proteins and enable integration of foreign sequences into the host genome for stable propagation. (See, e.g., Ausubel, 1995, supra; Bitter, G. A. et al. (1987) Methods Enzymol. 153:516-544; and Scorer, C. A. et al. (1994) Bio/Technology 12:181-184).

In a further aspect of the invention, a plant system may also be used for expression of Dre polypeptides. Transcription of nucleotide sequences encoding the subject polypeptide may be driven by viral promoters, e.g., the 35S and 19S promoters of CaMV used alone or in combination with the omega leader sequence from TMV (Takamatsu, N. (1987) EMBO J. 6:307-311). Alternatively, plant promoters such as the small subunit of RUBISCO or heat shock promoters may be used. (See, e.g., Coruzzi, G. et al. (1984) EMBO J. 3:1671-1680; Broglie, R. et al. (1984) Science 224:838-843; and Winter, J. et al. (1991) Results Probl. Cell Differ. 17:85-105). These constructs can be introduced into plant cells by direct DNA transformation or pathogen-mediated transfection. (See, e.g., The McGraw Hill Yearbook of Science and Technology (1992) McGraw Hill, New York N.Y., pp. 191-196).

An additional aspect of the invention contemplates the use of a mammalian system for expression of Dre polypeptides. In mammalian cells, a number of viral-based expression systems may be utilized. For example, in cases where an adenovirus is used as an expression vector, nucleotide sequences may be ligated into an adenovirus transcription/translation complex consisting of the late promoter and tripartite leader sequence. Insertion in a non-essential E1 or E3 region of the viral genome may be used to obtain infective virus that will express the subject polypeptide in host cells. (See, e.g., Logan, J. and T. Shenk (1984) Proc. Natl. Acad. Sci. USA 81:3655-3659). In addition, transcription enhancers, such as the Rous sarcoma virus (RSV) enhancer, may be used to increase expression in mammalian host cells. SV40 or EBV-based vectors may also be used for high-level protein expression.

Alternatively, human artificial chromosomes (HACs) may also be employed to deliver larger fragments of nucleotide sequence than can be contained in and expressed from a plasmid. HACs of about 6 kb to 10 Mb are constructed and delivered via conventional delivery methods (liposomes, polycationic amino polymers, or vesicles) for therapeutic purposes. (See, e.g., Harrington, J. J. et al. (1997) Nat. Genet. 15:345-355).

For long term production of recombinant proteins in mammalian systems, stable expression of Dre polypeptides in cell lines is preferred. For example, nucleotide sequences encoding Dre polypeptides can be transformed into cell lines using expression vectors that may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells that successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk$^-$ and apr$^-$ cells, respectively. (See, e.g., Wigler, M. et al. (1977) Cell 11:223-232; Lowy, I. et al. (1980) Cell 22:817-823.) Also, antimetabolite, antibiotic, or herbicide resistance can be used as the basis for selection. For example, dhfr confers resistance to methotrexate; neo confers resistance to the aminoglycosides neomycin and G-418; and als and pat confer resistance to chlorsulfuron and phosphinotricin acetyltransferase, respectively. (See, e.g., Wigler, M. et al. (1980) Proc. Natl. Acad. Sci. USA 77:3567-3570; Colbere-Garapin, F. et al. (1981) J. Mol. Biol. 150:1-14). Additional selectable genes have been described, e.g., trpB and hisD, which alter cellular requirements for metabolites. (See, e.g., Hartman, S. C. and R. C. Mulligan (1988) Proc. Natl. Acad. Sci. USA 85:8047-8051). Visible markers, e.g., anthocyanins, green fluorescent proteins (GFP; Clontech), β-glucuronidase and its substrate β-glucuronide, or luciferase and its substrate luciferin may be used. These markers can be used not only to identify transformants, but also to quantify the amount of transient or stable protein expression attributable to a specific vector system. (See, e.g., Rhodes, C. A. (1995) Methods Mol. Biol. 55:121-131).

Although the presence/absence of marker gene expression suggests that the nucleotide sequence of interest is also present, the presence and expression of the gene may need to be confirmed. For example, if the sequence encoding a Dre polypeptide is inserted within a marker gene sequence, transformed cells containing the subject polypeptide can be identified by the absence of marker gene function. Alternatively, a marker gene can be placed in tandem with a sequence encoding a subject polypeptide under the control of a single promoter. Expression of the marker gene in response to induction or selection usually indicates expression of the tandem gene as well.

Generally speaking, host cells that contain the nucleotide sequence encoding Dre polypeptides may be identified by a variety of procedures known to those of skill in the art. These procedures include, but are not limited to, DNA-DNA or DNA-RNA hybridizations, PCR amplification, and protein bioassay or immunoassay techniques that include membrane, solution, or chip based technologies for the detection and/or quantification of nucleic acid or protein sequences.

Host cells transformed with nucleotide sequences encoding Dre polypeptides may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing the subject nucleotide sequence may be designed to contain signal sequences that direct secretion of the subject polypeptides through a prokaryotic or eukaryotic cell membrane.

In addition, a host cell strain may be chosen for its ability to modulate expression of the inserted nucleotide sequences or to process the expressed protein in the desired fashion. Such modifications of the polypeptide include, but are not limited to, acetylation, carboxylation, glycosylation, phosphorylation, lipidation, and acylation. Post-translational processing that cleaves a "prepro" or "pro" form of the protein may also be used to specify protein targeting, folding, and/or activity. Different host cells that have specific cellular machinery and characteristic mechanisms for post-translational activities (e.g., CHO, HeLa, MDCK, HEK293, and W138) are available from the American Type Culture Collection (ATCC, Manassas Va.) and may be chosen to ensure the correct modification and processing of the foreign protein.

Rox Site and Lox Site Nucleotide Sequences

The invention also encompasses a rox nucleotide sequence. The rox sites typically function as substrate sites for the Dre recombinase having SEQ ID NO. 1. The Dre recombinase of the invention catalyzes site specific recombination at a rox site that is not recognized by wild-type Cre or other Cre homologues of the invention having SEQ ID Nos. 2, 3, or 4. Conversely, Dre recombinase does not catalyze site specific recombination at a lox site. The rox site of the invention consists of two 14 base pair inverted repeats separated by a 4 base pair spacer region and has the following nucleotide sequence:

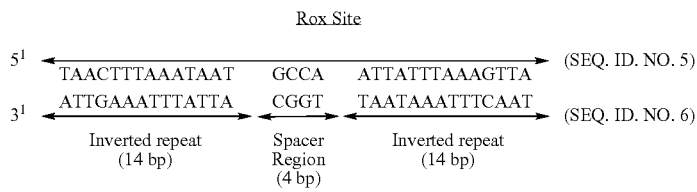

A further aspect of the invention encompasses the use of lox site nucleotide sequences. The lox sites typically function as a substrate for the Cre homlogues of the invention having SEQ ID Nos. 2, 3, or 4. In general, lox site nucleotide sequences will typically consist of two oppositely oriented perfect repeats that are separated by a spacer region. For example, the loxP site consists of two 13 base pair inverted repeats separated by an 8 base pair spacer region. Lox sites suitable for use in the practice of the invention include any of loxP, loxB, loxL, or loxR. In a preferred embodiment, the lox site will be a loxP site having the following nucleotide sequence:

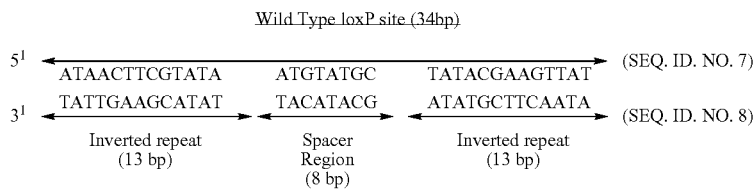

The rox and lox sites may be produced by a number of methods generally known in the art or as described in the examples herein. For example, rox and lox sites can be produced by a variety of synthetic techniques that are known in the art, such as the synthetic techniques for producing lox sites described by Ito et al. (1982) Nuc. Acid Res., 10: 1755; and Ogilvie et al., (1981) Science, 214: 270.

Dre/rox and Cre/lox Systems

Another aspect of the invention encompasses a Dre/rox system. The system typically comprises the Dre recombinase having SEQ ID NO. 1 and at least one rox site. The novel Dre/rox system may be used alone or in combination with other Cre/lox systems currently known in the art. A number of methods utilizing the Dre/rox system of the invention are described in detail below.

An additional aspect of the invention encompasses a Cre homologue/lox system. The system generally comprises a Cre homologue of the invention having any of SEQ ID Nos. 2, 3, or 4 in combination with at least one lox site. The Cre homologue/lox system may be used in place of the wild-type Cre/lox system in any of the application detailed herein or otherwise known in the art.

Methods Using the Dre/rox System

The Dre/rox system of the invention may be utilized in several applications, including for conditional mutagenesis and gene expression, gene replacement and deletion, and chromosome engineering. These applications are described more fully below.

It is contemplated that the rox sites of the invention may be introduced into a nucleic acid in a number of different orientations in order to achieve a desired recombination result for any given application. Since a rox site is an asymmetrical nucleotide sequence, two rox sites on the same DNA molecule can have the same or opposite orientation with respect to each other. In one embodiment, recombination between rox sites in the same orientation results in a deletion of the DNA segment located between the two rox sites and a connection between the resulting ends of the original DNA molecule. The deleted DNA segment forms a circular molecule of DNA. The original DNA molecule and the resulting circular molecule each contain a single rox site. Alternatively, recombination between two rox sites in opposite orientations on the same DNA molecule result in an inversion of the nucleotide sequence of the DNA segment located between the two rox sites. In addition, reciprocal exchange of DNA segments proximate to rox sites located on two different DNA molecules can occur.

One embodiment encompasses use of the Dre/rox system of the invention in a method for producing a site-specific recombination in a nucleotide sequence having a target DNA segment. In this method, a first and second rox site of the invention is introduced into the nucleotide sequence such that the rox sites flank the target DNA segment. The nucleotide sequence may be either in vitro, such as a plasmid in a reaction tube, or it may be in vivo, such as in a cell. The target DNA segment can be a gene or a number of other sequences of deoxyribonucleotides of homologous, heterologous or synthetic origin. In an exemplary embodiment, the target DNA segment is a gene for a structural protein, an enzyme, a regulatory molecule; or a DNA sequence that influences gene expression in the cell such as a regulatory nucleotide sequence, a promoter, or a polyadenylation nucleotide sequence. The nucleotide sequence comprising the target DNA segment flanked by the first and second rox sites are then contacted with a Dre polypeptide of the invention. The contact may take place either in vitro or in vivo. In a preferred embodiment, the Dre polypeptide will be contacted with the rox sites as a Dre nucleotide sequence operably linked to an inducible regulatory sequence, such as any of the inducible promoters described above or otherwise generally known in the art, so that its expression can be triggered at a desired time. Alternatively, the Dre polypeptide can be contacted with the rox sites according to the methods described herein or generally known in the art. In one alternative of this embodiment, the first and second rox sites have the same orientation, and contact with Dre produces a deletion of the target DNA segment. Alternatively, in another embodiment the first and second rox sites have opposite orientation, and contact with Dre produces an inversion of the nucleotide sequence of the target DNA segment. In still another alternative of this embodiment, the first and second rox sites are introduced into two different nucleotide sequences and contact with the Dre produces a reciprocal exchange of nucleotide sequence proximate to the rox sites.

Yet another preferred embodiment encompasses use of the Dre/rox system of the invention in a method comprising a means to selectively produce site-specific recombination in a number of different nucleotide sequences. Because Dre and Cre are heterospecific recombinases, a Dre/rox system and a Cre/lox system may be used together in a method for selectively producing site-specific recombination. For example, the method may comprise producing site-specific recombination at multiple different nucleotide sequences or at one or more sites within the same nucleotide sequence. The nucleotide sequences may be either in vitro, such as in a test tube, or it may be in vivo, such as the same cell or in a combination of different cells. By way of non-limiting example, when the method has two nucleotide sequences it typically will employ one Dre polypeptide and one Cre polypeptide. The Dre polypeptide recognizes rox sites, but not lox sites. The Cre polypeptide recognizes lox sites but not rox sites. Advantageously, because Dre and Cre are heterospecific, the method provides a means to selectively catalyze site-specific recombination at the two target DNA segments either simultaneously or at different times. A method for producing site-specific recombination at two target DNA segments is described in detail below.

Accordingly, in one alternative of this embodiment site-specific recombination is selectively performed at a first and a second nucleotide sequence. The method employs two rox sites, two lox sites, a Dre recombinase and a Cre recombinase. In this embodiment, a first and second rox site is introduced into the first nucleotide sequence such that the rox sites flank a first target DNA segment. The method also encompasses introducing a first and a second lox site into a second nucleotide sequence such that the lox sites flank a second target DNA segment. The first and second lox sites comprise a wild-type lox site such as any of loxP, loxB, loxL, or loxR. In a typical embodiment, the first and second lox sites comprise wild-type loxP. Depending upon the embodiment, the lox sites may be introduced into either the same nucleotide sequence as the rox sites or into different nucleotide sequence. The method additionally comprises contacting the rox sites with Dre polypeptide and contacting the lox sites with Cre polypeptide. The Dre and Cre polypeptides typically will be contacted with the nucleotide sequence comprising either the rox sites or lox sites as a Dre nucleotide sequence operably linked to an inducible regulatory sequence or as a Cre nucleotide sequence operably linked to an inducible regulatory sequence, such as any of the inducible promoters described above or otherwise generally known in the art, so that recombinase expression can be triggered at a desired time. Alternatively, the Dre or Cre polypeptides can be contacted with the nucleotide sequence comprising the rox sites or lox sites according to the methods described herein or generally known in the art. Depending upon the particular embodiment, the rox sites may be contacted with the Dre polypeptide either before, simultaneously, or after the lox sites are contacted with the Cre polypeptide. In one alternative of this embodiment, the rox sites and lox sites have the same orientation relative to each other, and contact with the particular Dre or Cre polypeptide produces a deletion of the respective target DNA segment. Alternatively, in another embodiment the rox sites and the lox sites have opposite orientation relative to each other, and contact with the particular Dre or Cre polypeptide produces an inversion of the nucleotide sequence of the respective target DNA segment. In still another alternative of this embodiment, the rox sites are each introduced into two different nucleotide sequences and contact with the particular Dre polypeptide produces a reciprocal exchange of nucleotide sequence proximate to the rox sites. In an additional embodiment, the rox sites are introduced in opposite orientation and the pair of lox sites is introduced in the same orientation. In still another embodiment, the rox sites are introduced in opposite orientation and the lox sites are introduced on two separate nucleotide sequences. In yet another embodiment, the rox sites are introduced in the same orientation and the lox sites are introduced on two separate nucleotide sequences.

In one exemplary application, the methods of the invention will be utilized to knock-in a target DNA segment, such as a gene, by use of a site-specific recombination reaction that is catalyzed by a Dre polypeptide of the invention. One preferred use for the knock-in embodiment, is for introduction of a target DNA segment into a chromosome or into a transgenic animal, such as a mouse. In this method, a first nucleotide construct comprising a nucleotide sequence encoding a Dre polypeptide operably linked to a promoter is used to site-specifically recombine a second nucleotide construct comprising two rox sites, a target DNA segment to be knocked-in, and a promoter. In a typical embodiment, the promoter employed to express the Dre polypeptide will be an inducible promoter so that the target DNA segment can be knocked-in by the Dre at a time and location controlled manner. In a typical arrangement of the second nucleotide construct, the promoter is arranged upstream of a first rox site and the second rox site is downstream of the first rox site, with an intervening nucleotide sequence disposed between the first and second rox sites. The promoter is preferably arranged so as to induce the expression of the target DNA segment to be knocked-in. An exemplary second nucleotide construct has the following arrangement:

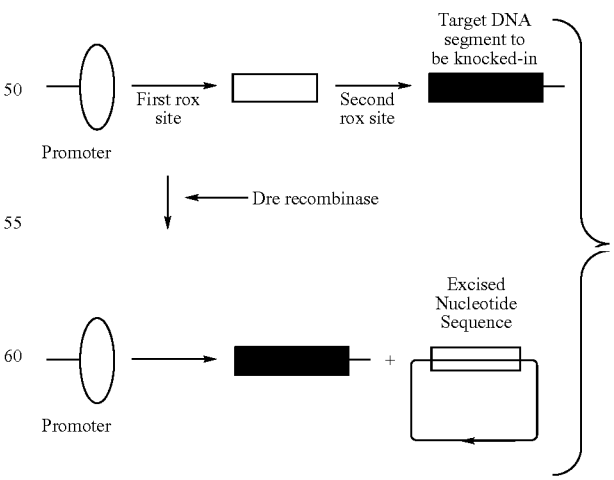

When the Dre polypeptide is contacted with the rox sites, it binds to the sites and removes the intervening nucleotide sequence disposed between the first and second rox sites (see diagram above). After the Dre polypeptide has excised the intervening nucleotide sequence, the first rox site is left behind and the target DNA segment is operably linked to the promoter in a manner such that the promoter can cause expression of the target DNA segment.

Alternatively, in yet another exemplary application, the methods of the invention will be utilized to knock-out a target DNA segment, such as a gene, by use of a site-specific recombination reaction that is catalyzed by a Dre polypeptide of the invention. The method is typically employed to terminate expression of a gene. In many respects, the knocking-out method is performed in a substantially similar manner as the knocking-in method except the position of the promoter sequence in relation to the target DNA segment in the second nucleotide construct is different. Because the knocking-out method is employed primarily as a means to terminate gene expression, it is satisfactory if either the target DNA segment or the promoter sequence are knocked-out, either in whole or in part, from the second nucleotide construct. Suitable examples of arrangements for the first and second rox sites, the promoter sequence, and the target DNA segment within the second nucleotide construct are included in examples (a), (b) or (c):

(a) —promoter—first rox site—target DNA segment—second rox site—
(b) —first rox site—promoter—target DNA segment—second rox site—
(c) —first rox site—promoter—second rox site—target DNA segment—

The knock-out method also encompasses a first nucleotide construct comprising a nucleotide sequence encoding a Dre polypeptide operably linked to a promoter. In a typical embodiment, the promoter employed to express the Dre polypeptide will be an inducible promoter so that the target DNA segment can be knocked-out by the Dre at a time and location controlled manner. When the Dre polypeptide is contacted with the rox sites, it binds to the sites and removes the intervening nucleotide sequence disposed between the first and second rox sites. Depending upon the arrangement of the second nucleotide construct, the intervening nucleotide sequence may include all or a part of the promoter or the target DNA segment, or both. This nucleotide sequence excision results in a loss of target DNA segment function, or loss of promoter function or both. A schematic showing a typical embodiment of knock-out of a target DNA segment is as follows:

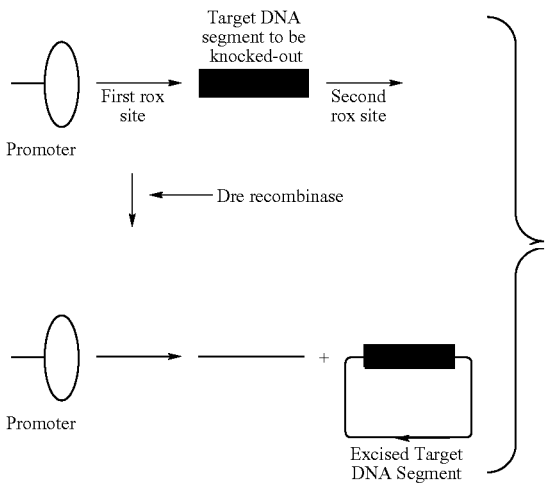

The knock-in and knock-out methods described above may be utilized to introduce or excise a target DNA segment in a variety of in vivo or in vitro applications and in several organisms. By way of non-limiting example, the methods may be employed as a tool for conditional mutagenesis and gene expression, gene replacement and deletion, and chromosome engineering.

In one exemplary embodiment, the knock-in and knock-out methods are employed to produce a variety of transgenic non-human organisms. The transgenic organisms may be produced by the methods described herein or methods that are generally known in the art, such as by using homologous recombination in embryonic stem cells (See, e.g., U.S. Pat. Nos. 5,175,383 and 5,767,337.). For example when utilizing a knock-out method, mouse embryonic stem (ES) cells, such as the mouse 129/SvJ cell line, are derived from the early mouse embryo and grown in culture. Homologous recombination takes place using the Dre/rox system of the invention to knock-out a gene of interest in a tissue- or developmental stage-specific manner, as described above or as known in the art (Marth, J. D. (1996) Clin. Invest. 97:1999-2002; Wagner, K. U. et al. (1997) Nucleic Acids Res. 25:4323-4330). Transformed ES cells are identified and microinjected into mouse cell blastocysts such as those from the C57BL/6 mouse strain. The blastocysts are surgically transferred to pseudopregnant dams, and the resulting chimeric progeny are genotyped and bred to produce heterozygous or homozygous strains. Alternatively, when utilizing a knock-in method, polynucleotides encoding a target DNA segment can be used to create transgenic animals (mice or rats). Typically, a region of a polynucleotide encoding a target DNA segment is injected into animal embryonic stem cells, and the injected sequence integrates into the animal cell genome. Transformed cells are injected into blastulae, and the blastulae are implanted as described above.

Figure 8:
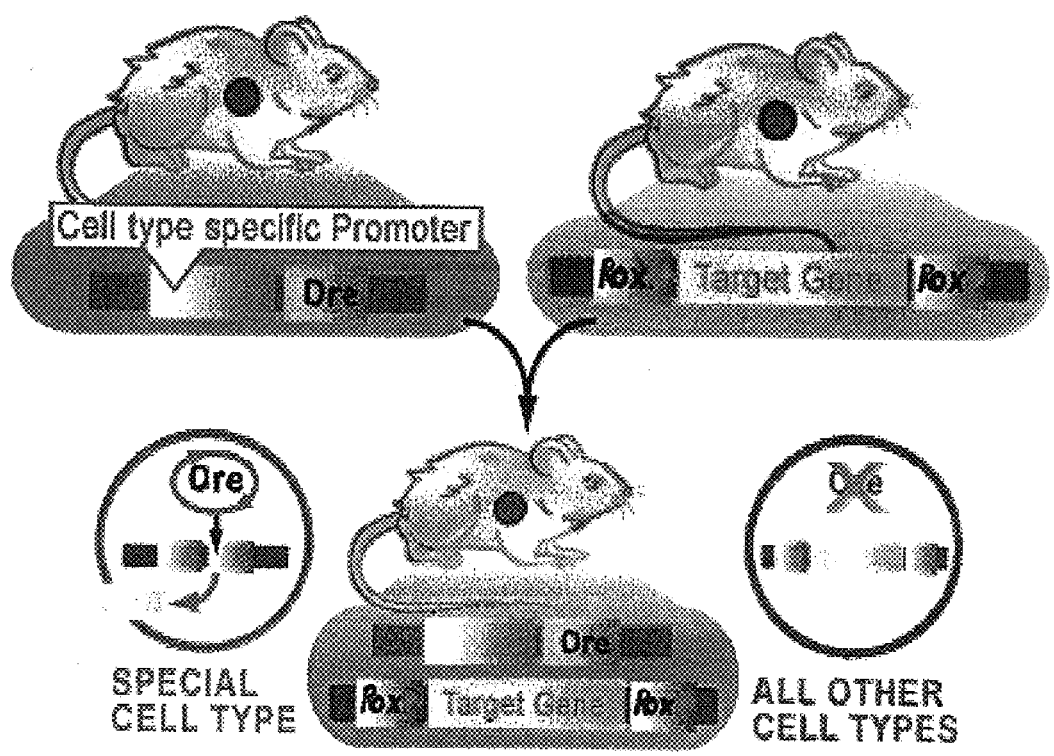
FIG. 8 is a schematic illustrating use of the Dre/rox system in transgenic mice. Mice with Dre protein expression in a specific cell type are bred to mice that contain a target gene surrounded by rox sites. When the mice are bred, the cells carrying Dre will those cells to lose the target gene.

In one non limiting example of a transgenic animal that may be produced in the practice of the invention, a knock-out mouse that no longer has a target gene in a particular cell type can be produced. Referring to FIG. 8, a transgenic mouse containing a target gene flanked by rox sites is mated with a transgenic mouse that expresses a Dre recombinase gene in only one cell type. The mouse resulting from this breeding will have both the Dre gene and the rox-flanked gene. In cells of the mouse that does not express the Dre polypeptide, the target gene will function normally. Alternatively, in a cell where the Dre is expressed, the target gene will be deleted. In a preferred alternative of this embodiment, the target gene will be conditionally knocked-out. A conditional knock-out mouse can be produced if the Dre gene is operably linked to an inducible or tissue specific promoter. When conditions needed for promoter function are provided, Dre polypeptide is expressed and the target gene is knocked out. Alternatively, if conditions needed for promoter function are not provided, Dre polypeptide is not expressed and the target gene is not knocked-out.

Introduction of Dre and Cre Sequences and rox and lox Sequences

Irrespective of the particular use of the Dre/rox system of the invention, a number of methods are suitable for introducing rox or lox site nucleotide sequences and Dre or Cre nucleotide sequences into a nucleic acid molecule or a target cell. The method selected for such introduction can and will vary depending upon the particular sequence and target cell. Generally speaking, the cell may be an in vivo or in vitro cell. For example, the nucleotide sequences can be expressed by a recombinant cell, such as a bacterial cell, a cultured eukaryotic cell, or a cell disposed in a living organism, including a non-human transgenic organism, such as a transgenic animal.

By way of non-limiting example, cultured cells available for use include Hela cells, HEK 293 cells and U937 cells, as well as other cells used to express proteins.

In one exemplary embodiment of the invention, a vector, such as a vector detailed above, can be employed to introduce a suitable rox or lox site or Dre or Cre polynucleotide into a host cell. Typically, in this aspect of the invention, the polynucleotide is incorporated into an expression vector, which subsequently is utilized to transfect a target cell. Depending upon the embodiment, the cell may be a cultured cell or a cell disposed within a living organism. Irrespective of the embodiment, the vector binds to the target cell membrane, and the subject nucleotide sequence is internalized into the cell. The vector comprising the nucleotide sequence (i.e., rox or lox site or Dre or Cre) may be either integrated into the target cell's nucleic acid sequence or may be a plasmid. Irrespective of its form, the vector employed results in Dre or Cre polypeptide expression and insertion of the rox or lox sites at a desired location.

In one embodiment, the transfer vector is a retrovirus. Retroviruses can package up to 5 Kb of exogenous nucleic acid material, and can efficiently infect dividing cells via a specific receptor, wherein the exogenous genetic information is integrated into the target cell genome. In the host cell cytoplasm, the reverse transcriptase enzyme carried by the vector converts the RNA into proviral DNA, which is then integrated into the target cell genome, thereby expressing the transgene product.

In another alternative embodiment, the transfer vector is an adenovirus. In general, adenoviruses are large, double-stranded DNA viruses which contain a 36 Kb genome that consists of genes encoding early regulatory proteins and a late structural protein gene. Adenoviruses, advantageously, can be grown in high titers of purified recombinant virus (up to $10^{12}$ infectious particles/ml), incorporate large amounts of exogenous genetic information, and can broadly infect a wide range of differentiated non-dividing cells in vivo.

In yet another alternative embodiment, the transfer vector is an adeno-associated virus (AAV). AAV is a human parvovirus that is a small, single-stranded DNA virus that can infect both dividing and non-dividing cells. AAV is relatively non-toxic and non-immunogenic and results in long-lasting expression. The packaging capacity of recombinant AAV is 4.9 kb. Successful AAV-mediated gene transfer into brain, muscle, heart, liver, and lung tissue has been reported.

Exemplary transfer vectors for transfer into eukaryotic cells include MSCV, Harvey murine sarcoma virus, pFast-Bac, pFastBac HT, pFastBac DUAL, pSFV, pTet-Splice, pEUK-Cl, pPUR, pMAM, pMAMneo, pBI101, pBI121, pDR2, pCMVEBNA, YACneo, pSVK3, pSVL, pMSG, pCH110, pKK232-8, p3'SS, pBlueBacIII, pCDM8, pcDNA1, pZeoSV, pcDNA3, pREP4, pET21b, pCEP4, and pEBVHis vectors.

In one embodiment and by way of non limiting example, the vector will be the $Ap^R$ reporter plasmid. Briefly, the $Ap^R$ plasmid carries two directly repeated rox sites flanking a rrn T1T2 transcription terminator (Term) interposed between the lac promoter and neo. Dre-mediated excision at the rox sites allows neo expression to give kanamycin resistance.

The transfected cells include isolated in vitro population of cells. In vivo, the vector can be delivered to selected cells, whereby the carrier for the vector is attracted to the selected cell population.

Activation of the gene in a transfected cell can be caused by an external stress factor. For example, the transfected cells can be contacted with an etoposide or a proteosome inhibitor.

In the alternative, an activator can be included in the vector in accordance with the methods detailed above.

In another alternative embodiment, the rox site, lox site, Cre or Dre nucleotide sequences can be introduced into a target cell by mechanical, electrical or chemical procedures. Mechanical methods include microinjection, pressure, and particle bombardment. Electrical methods include electroporation. Chemical methods include liposomes, DEAE-dextran, calcium phosphate, artificial lipids, proteins, dendrimers, or other polymers, including controlled-release polymers.

In one aspect of this embodiment, accordingly, a mechanical method is employed to introduce the subject nucleotide sequences into the target cell. One such method is hydrodynamic force and other external pressure-mediated DNA transfection methods. Alternatively, ultrasonic nebulization can be utilized for DNA-lipid complex delivery. In other suitable embodiments, particle bombardment, also known as biolistical particle delivery, can be utilized to introduce DNA into several cells simultaneously. In still another alternative mechanical method, DNA-coated microparticles (e.g., gold, tungsten) are accelerated to high velocity to penetrate cell membranes or cell walls. This procedure is used predominantly in vitro for adherent cell culture transfection.

In a further aspect of this embodiment, an electrical method is employed to introduce subject nucleotide sequences into the target cell. In one alternative of this embodiment, electroporation is employed. Electroporation uses high-voltage electrical impulses to transiently permeabilize cell membranes, and thereby, permits cellular uptake of macromolecules, such as nucleic acid and polypeptide sequences.

In an additional aspect of this embodiment, a chemical method is employed to introduce a selected nucleotide sequences into the target cell. Chemical methods, using uptake-enhancing chemicals, are highly effective for delivering nucleic acids across cell membranes. For example, nucleotide sequences are typically negatively charged molecules. DEAE-dextran and calcium phosphate, which are positively charged molecules, interact with nucleotide sequences to form DEAE-dextran-DNA and calcium phosphate-DNA complexes, respectively. These complexes are subsequently internalized into the target cell by endocytosis.

In another alternative embodiment, the chemical enhancer is lipofectin-DNA. This complex comprises an artificial lipid-based DNA delivery system. In this embodiment, liposomes (either cationic, anionic, or neutral) are complexed with DNA. The liposomes can be used to enclose a subject nucleic acid for delivery to target cells, in part, because of increased transfection efficiency.

In yet another alternative chemical embodiment, protein-based methods for DNA introduction may also utilized. The cationic peptide poly-L-lysine (PLL) can condense DNA for more efficient uptake by cells. Protamine sulfate, polyamidoamine dendrimers, synthetic polymers, and pyridinium surfactants may also be utilized.

In still a further chemical embodiment for nucleotide introduction, biocompatible controlled-release polymers may be employed. Biodegradable poly (D,L-lactide-co-glycolide) microparticles and PLGA microspheres have been used for long-term controlled release of DNA molecules to cells. In a further embodiment, the subject nucleotide sequences may also be encapsulated into poly(ethylene-co-vinyl acetate) matrices, resulting in long term controlled, predictable release for several months.

Similarly, as for the introduction of Dre or Cre nucleotide sequences, the Dre or Cre polypeptide can also be introduced into target cells by any of the mechanical, electrical or chemical means detailed above. Mechanical methods include microinjection, pressure, and particle bombardment. Direct microinjection of Dre polypeptide into cells in vitro occurs directly and efficiently. As with DNA-injected cells, once cells are modified in vitro, they can be transferred to the in vivo host environment. In particle bombardment, Dre polypeptide-coated microparticles are physically hurled with force against cell membranes or cell walls to penetrate cells in vitro. Electroporation, particularly at low voltage, and high frequency electrical impulses, is suitable for introduction of Dre polypeptides with in vitro or in vivo. Moreover, any of the chemical means detailed above may also be employed.

The invention also encompasses nucleic acid constructs, cells and organisms having a Dre recombinase (i.e., nucleotide or polypeptide), rox or lox site, or both a Dre and rox site.

Production of Antibodies Specific for Dre Polypeptide

Yet a further aspect of the invention encompasses the use of Dre polypeptides or proteins to produce antibodies. The antibodies may be employed in in vitro and in vivo assays or to purify a Dre polypeptide. Antibodies to any of the polypeptides suitable for use in the invention may be generated using methods that are well known in the art. Such antibodies may include, but are not limited to, polyclonal, monoclonal, chimeric, and single chain antibodies, Fab fragments, and fragments produced by a Fab expression library.

For the production of antibodies, various hosts including goats, rabbits, rats, mice, humans, and others may be immunized by injection with a subject polypeptide that has immunogenic properties. Depending on the host species, various adjuvants may be used to increase immunological response. Such adjuvants include, but are not limited to, Freund's, mineral gels such as aluminum hydroxide, and surface-active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to a selected polypeptide have an amino acid sequence consisting of at least about 5 amino acids, and generally will consist of at least about 10 amino acids. It is also preferable that these oligopeptides, peptides, or fragments are identical to a portion of the amino acid sequence of the natural protein. Short stretches of the selected polypeptide's amino acid may be fused with those of another protein, such as KLH, and antibodies to the chimeric molecule may be produced.

Monoclonal antibodies to a polypeptide may be prepared using a technique that provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495-497; Kozbor, D. et al. (1985) J. Immunol. Methods 81:3142; Cote, R. J. et al. (1983) Proc. Natl. Acad. Sci. USA 80:2026-2030; and Cole, S. P. et al. (1984) Mol. Cell Biol. 62:109-120.)

In addition, techniques developed for the production of "chimeric antibodies," such as the splicing of mouse antibody genes to human antibody genes to obtain a molecule with appropriate antigen specificity and biological activity can be used. (See, e.g., Morrison, S. L. et al. (1984) Proc. Natl. Acad. Sci. USA 81:6851-6855; Neuberger, M. S. et al. (1984) Nature 312:604-608; and Takeda, S. et al. (1985) Nature 314:452-45). Alternatively, techniques described for the production of single chain antibodies may be adapted, using methods known in the art, to produce Dre polypeptide-specific single chain antibodies. Antibodies with related specificity, but of distinct idiotypic composition, may be generated by chain shuffling from random combinatorial immunoglobulin libraries. (See, e.g., Burton, D. R. (1991) Proc. Natl. Acad. Sci. USA 88:10134-10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. USA 86:3833-3837; Winter, G. et al. (1991) Nature 349:293-299.)

Antibody fragments that contain specific binding sites for Dre polypeptides may also be generated. For example, such fragments include, but are not limited to, $F(ab')_2$ fragments produced by pepsin digestion of the antibody molecule and Fab fragments generated by reducing the disulfide bridges of the $F(ab')_2$ fragments. Alternatively, Fab expression libraries may be constructed to allow rapid and easy identification of monoclonal Fab fragments with the desired specificity. (See, e.g., Huse, W. D. et al. (1989) Science 246:1275-1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between the polypeptide and its specific antibody. A two-site, monoclonal-based immunoassay utilizing monoclonal antibodies reactive to two non-interfering polypeptide epitopes is generally used, but a competitive binding assay may also be employed.

Various methods such as Scatchard analysis in conjunction with radioimmunoassay techniques may be used to assess the affinity of antibodies for the subject polypeptide. Affinity is expressed as an association constant, $K_a$, which is defined as the molar concentration of polypeptide-antibody complex divided by the molar concentrations of free antigen and free antibody under equilibrium conditions. The $K_a$ is determined for a preparation of polyclonal antibodies, which are heterogeneous in their affinities for multiple polypeptide epitopes, represents the average affinity, or avidity, of the antibodies for the particular polypeptides. The $K_a$ is determined for a preparation of monoclonal antibodies, which are monospecific for a particular polypeptide epitope, represents a true measure of affinity. High-affinity antibody preparations with $K_a$ ranging from about $10^9$ to $10^{12}$ L/mole are preferred for use in immunoassays in which the polypeptide-antibody complex must withstand rigorous manipulations. Low-affinity antibody preparations with $K_a$ ranging from about $10^6$ to $10^7$ L/mole are preferred for use in immunopurification and similar procedures that ultimately require dissociation of polypeptides, preferably in active form, from the antibody (Catty, D. (1988) Antibodies, Volume I: A Practical Approach, IRL Press, Washington D.C.; Liddell, J. E. and A. Cryer (1991) A Practical Guide to Monoclonal Antibodies, John Wiley & Sons, New York N.Y.).

The titer and avidity of polyclonal antibody preparations may be further evaluated to determine the quality and suitability of such preparation for certain downstream applications. For example, a polyclonal antibody preparation containing at least 1-2 mg specific antibody/ml, preferably 5-10 mg specific antibody/ml, is generally employed in procedures requiring precipitation of a subject polypeptide-antibody complex. Procedures for evaluating antibody specificity, titer, and avidity, and guidelines for antibody quality and usage in various applications, are generally available. (See, e.g., Catty, supra, and Coligan et al. supra.)

Generally speaking, the antibodies of the invention may be utilized in a variety of applications such as for protein purification. Alternatively, the antibodies are also used as tools to mark the presence of the Dre protein. The marker antibodies include a marker, such as a fluorescent marker, and will bind to the Dre protein.

Kits

A further aspect of the invention encompasses kits that employ the Dre/rox system of the invention.

In one embodiment, the kit is for producing site-specific recombination of a target DNA segment. Typically, a kit in this embodiment will include a purified Dre polypeptide that can catalyze site specific recombination at a rox site. The kit also comprises two isolated mutant rox nucleotide sequences. The kit will also include instructions for producing site-specific recombination of a target DNA segment.

In yet another embodiment, the kit is for producing selective site-specific recombination of two or more different target DNA segments. The kit comprises a purified Dre polypeptide, a purified Cre polypeptide, an isolated pair of rox nucleotide sequences, and an isolated pair of lox nucleotide sequences. The kit will also include instructions for producing selective site-specific recombination in the target DNA segments.

All publications, patents, patent applications and other references cited in this application are herein incorporated by reference in their entirety as if each individual publication, patent, patent application or other reference were specifically and individually indicated to be incorporated by reference.

DEFINITIONS

Cell as used herein refers to either a prokaryotic cell or an eukaryotic cell. Examples of such cells include bacterial cells, yeast cells, mammalian cells, plant cells, insect cells or fungal cells.

Conservative amino acid substitutions are those substitutions that do not abolish the ability of a subject polypeptide to participate in the biological functions as described herein. Typically, a conservative substitution will involve a replacement of one amino acid residue with a different residue having similar biochemical characteristics such as size, charge, and polarity versus non polarity. A skilled artisan can readily determine such conservative amino acid substitutions.

DNA segment refers to a linear fragment of single- or double-stranded deoxyribonucleic acid (DNA), which can be derived from any source.

The term expression as used herein is intended to mean the synthesis of gene product from a gene coding for the sequence of the gene product. The gene product can be RNA or a protein.

A gene is a hereditary unit that has one or more specific effects upon the phenotype of the organism that can mutate to various allelic forms.

Homology describes the degree of similarity in nucleotide or protein sequences between individuals of the same species or among different species. As the term is employed herein, such as when referring to the homology between either two proteins or two nucleotide sequences, homology refers to molecules having substantially the same function, but differing in sequence. Most typically, the two homologous molecules will share substantially the same sequence, particularly in conserved regions, and will have sequence differences in regions of the sequence that does not impact function.

A host organism is an organism that receives a foreign biological molecule, including an antibody or genetic construct, such as a vector containing a gene. The organism may be either a prokaryote or an eukaryote. For example, the organism may be a bacteria, a yeast, a mammal, a plant, an insect, or a fungus.

As used herein the expression lox site means a nucleotide sequence at which the gene product of the cre gene, referred to herein as Cre, can catalyze a site-specific recombination. The loxP site is a 34 base pair nucleotide sequence that can be isolated from bacteriophage P1 by methods known in the art. One method for isolating a loxP site from bacteriophage P1 is disclosed by Hoess et al., Proc. Natl. Acad. Sci. USA, 79: 3398 (1982). The loxP site consists of two 13 base pair inverted repeats separated by an 8 base pair spacer region. Other suitable lox sites include loxB, loxL and loxR sites which are nucleotide sequences isolated from $E.$ $coli$. These sequences are disclosed and described by Hoess et al., Proc. Natl. Acad. Sci. USA, 79: 3398 (1982). Lox sites can also be produced by a variety of synthetic techniques that are known in the art. For example, synthetic techniques for producing lox sites are disclosed by Ito et al., Nuc. Acid Res., 10: 1755 (1982) and Ogilvie et al., Science, 214: 270 (1981).

Mutation is defined as a phenotypic variant resulting from a changed or new gene. Mutant is an organism bearing a mutant gene that expresses itself in the phenotype of the organism. Mutants include both changes to a nucleic acid sequence, as well as elimination of a sequence or a part of a sequence. In addition polypeptides can be expressed from the mutants.

A nucleic acid is a nucleotide polymer better known as one of the monomeric units from which DNA or RNA polymers are constructed, it consists of a purine or pyrimidine base, a pentose, and a phosphoric acid group.

P1-related phage is typically a phage having a similar DNA structure, life-style and immuno-crossreactivity to $E.$ $coli$ bacteriophage P1. Typically, P1 phages have several unique characteristics that define them as a class including: 1) they are temperate phages that can exist as an extrachromosomal replicon in its host; 2) their genomes are large, such as from about 80 to about 100 kb; and 3) they have structural proteins (e.g., capsid, tail) that are related.

Peptide is defined as a compound formed of two or more amino acids, with an amino acid defined according to standard definitions, such as is found in the book "A Dictionary of Genetics" by King and Stansfield.

Plasmids are double-stranded, closed DNA molecules ranging in size from 1 to 200 kilobases. Plasmids are incorporated into vectors for transfecting a host with a nucleic acid molecule.

A polypeptide is a polymer made up of less than 350 amino acids.

Protein is defined as a molecule composed of one or more polypeptide chains, each composed of a linear chain of amino acids covalently linked by peptide bonds. Most proteins have a mass between 10 and 100 kilodaltons. A protein is often symbolized by its mass in kDa.

Polyadenylation nucleotide sequence or polyadenylation nucleotide region refers to a nucleotide sequence usually located 3' to a coding region which controls the addition of polyadenylic acid to the RNA transcribed from the coding region in conjunction with the gene expression apparatus of the cell.

As used herein, the term promoter region refers to a sequence of DNA, usually upstream (5') of the coding sequence, which controls the expression of the coding region by providing the recognition for RNA polymerase and/or other factors required for transcription to start at the correct site. A "promoter fragment" constitutes a DNA sequence consisting of the promoter region. A promoter region can include one or more regions that control the effectiveness of transcription initiation in response to physiological conditions, and a transcription initiation sequence.

Regulatory nucleotide sequence as used herein, refers to a nucleotide sequence located proximate to a coding region whose transcription is controlled by the regulatory nucleotide sequence in conjunction with the gene expression apparatus of the cell. Generally, the regulatory nucleotide sequence is located 5' to the coding region. A promoter can include one or more regulatory nucleotide sequences.

As used herein, the expression site-specific recombination is intended to include the following three events: (1) deletion of a target DNA segment flanked by rox or lox sites, (2) inversion of the nucleotide sequence of a target DNA segment flanked by rox or lox sites, and (3) reciprocal exchange of DNA segments proximate to rox or lox sites located on different DNA molecules. It is to be understood that this reciprocal exchange of DNA segments can result in an integration event.

Substrate as used herein is a site within a nucleic acid sequence recognized by a particular recombinase, wherein the recombinase catalyzes site specific recombination. For example, the substrate for Dre recombinase is a rox site and the substrate for Cre recombinase is a lox site.

Target DNA segment as employed herein can be a gene or a number of other sequences of deoxyribonucleotides of homologous, heterologous or synthetic origin. In an exemplary embodiment, the target DNA segment is a gene for a structural protein, an enzyme, a regulatory molecule; or a DNA sequence that influences gene expression in the cell such as a regulatory nucleotide sequence, a promoter, or a polyadenylation nucleotide sequence.

A vector is a self-replication DNA molecule that transfers a DNA segment to a host cell.

Wild-type is the most frequently observed phenotype, or the one arbitrarily designated as "normal". Often symbolized by "+" or "WT."

As various changes could be made in the above compounds, products and methods without departing from the scope of the invention, it is intended that all matter contained in the above description and in the examples given below, shall be interpreted as illustrative and not in a limiting sense.

EXAMPLES

Examples 1-4 below detail the ability of Dre recombinase or Cre homologues to catalyze site specific recombination at either a rox site or at a lox site, depending upon the particular polypeptide.

In the examples below, where indicated, the following experimental procedures and reagents were employed:

Bacteria and Phage

Bacterial strains and lysogens used in these examples are listed in Table 1. Bacteria were propagated in Luria-Bertani broth (26) with appropriate antibiotics: streptomycin (10 μg/ml), ampicillin (100 μg/ml) and chloramphenicol (34 μg/ml). Zeocin (Invitrogen) was used at a concentration of 10 μg/ml in Lennox broth (27). Phage were titered, maintained and propagated in the presence of 5 mM $CaCl_2$. Lysogenization of DH5ΔlacU169 by selection for $Cm^R$ after infection with P1 CM (a gift from N. Sternberg) generated BS610.

In general, phage stocks were prepared and titered using the indicator strain Sh-16. Strains lysogenic for P1CM, P7 c1.9, φw39 and D6 (Table 1) all spontaneously released a low number of phage after culture overnight that gave small plaques on Sh-16, indicating that these P1-like phages were capable of both lysogenic and lytic growth. Phage plate stocks (9-10 hr at 37° C.) were prepared with a fresh overnight culture of the indicated donor strain (28), and used immediately. For transduction, 0.1 ml of a fresh overnight of the recipient strain DH5ΔlacU169 was infected with an aliquot of the transducing stock. After preadsorption for 5 min at room temperature, cells were diluted to 1 ml with Luria-Bertani broth +5 mM $CaCl_2$, incubated 50 min at 37° C. and then plated on selective medium.

DNA Sequencing and Plasmid Construction

Circular plasmid DNA of bacteriophages P1 CM, P7 c1.9, φw39, p15B and D6 was prepared using the Qiagen Large Construct Kit (Valencia, Calif.). For phages PICM, P7 c1.9, φw39 and p15B PCR primers were based on the published sequences of the P1 genes between lpa (formerly gene 10) and ref. This region encompasses the DNA packaging genes pacA and pacB, the c1 gene along with several other immunity genes, and the gene for Cre recombinase. For all of these phages at least several P1 primer pairs were identified for amplification of this interval. PCR fragments generated from each phage were sequenced directly and the resulting sequence information was used to design additional primers. A combination of PCR fragment sequencing and primer walking by direct sequencing from phage DNA was then used to obtain the complete sequence for each phage of the ~7 kb region from pacA to the beginning of the ref gene.

For phage D6 none of the PCR primer pairs used for P1 or the other P1-related phages produced an amplified product. A D6 library was constructed by partial Sau3A digestion of D6 DNA, cloning into the BamHI site of pUC19 and transformed into DH5α. To eliminate smaller clones from this library it was digested with EcoRI, size-selected by agarose gel electrophoresis to contain inserts of ≧1.5 kb and religated. Shotgun sequencing identified one clone having strong similarity to the P1 pacB gene. Specific primers were designed and were used to sequence directly from D6 DNA by primer walking in both directions to obtain ~7 kb of flanking sequence.

DNA sequences were assembled and analyzed using Vector NTI (Invitrogen) and then compared to the corresponding region of the P1 genome, GenBank accession number AF234172. The sequences of the immC regions of phages P7 c1.9 (6751 bp), φw39 (7208 bp), p15B (7094 bp) and D6 (7644 bp) have been assigned GenBank accession numbers AY751747, AY751748, AY751749 and AY753669, respectively.

Oligonucleotide sequencing primers and linkers were synthesized by Integrated DNA Technologies (Coralville, Iowa) and restriction enzymes were from New England Biolabs (Beverly, Mass.). Annealing of the oligo's 5'-CTA G ATAACTTTAAATAATTGGCATTATTTAAAGTTAG-3' (SEQ ID NO. 9) and 5'-GAT C CTAACTTTAAATAATGCCAATTATTTAAAGTTAT-3' (SEQ ID NO. 10) and cloning into the XbaI and BamHI sites of pUC19 generated the rox plasmid pBS1051 (D6 sequence underlined). Similarly, oligo's 5'-CTA GCT ATAACTTCGTATAATGTATGCTATACGAAG TTG-3' (SEQ ID NO. 11) and 5'-TCG AC AACTTCGTATAGCATACATTATACGAAGTTATAG-3' (SEQ ID NO. 12) were cloned into a pBluescript II KS (Stratagene) derivative using NheI and SalI to give the rox plasmid pBS516. The one nucleotide difference (double underline) of this rox site from rox does not affect Cre-mediated recombination (29). Digestion of pBS1051 with either XbaI+AlwNI or BamHI+AlwNI and ligation with the XbaI-BamHI zeo fragment from pZeoSV (Invitrogen) generated the $rox^2$-zeo plasmid pBS1080. The analogous rox² zeo plasmid pBS890 was constructed by blunt-ending the 600 bp FokI-SalI zeo fragment from pZeoSV and cloning it into the SmaI site of the rox² vector pBS246 (30). The dre gene was amplified with Pfu DNA polymerase (Stratagene) from D6 DNA with the oligo's 5'-AGA TGG TAC CAG GAG GAT ATC AAT ATGAGTGAATTAATTATCTCTGG-3' (SEQ ID NO. 13) and 5'-CTT TAG TCT AGA TTC A TTATGAATCCATCAAGCGGC-3' (SEQ ID NO. 14) (D6 coding region underlined), digested with KpnI and XbaI and cloned into the Cm$^R$ arabinose-inducible vector pBAD33 (31) to generate pBS1081. The analogous pBAD33-cre construct has been described previously (6). All cloned oligos and PCR products were confirmed by DNA sequencing.

The dre gene was placed under the control of the EF1α promoter for mammalian expression by replacing the KpnI-XbaI GFP fragment of pBS377 (32) with the KpnI-XbaI dre fragment from pBS1081. The EF1α-cre expression plasmid pBS513 (33) and the control CMV-lacZ plasmid p324 (34) have been described previously. To construct the EGFP expression vector pBS504 the following three DNA fragments were cloned between the unique HindIII and EcoRI sites of pBS397 (35): the EcoRI-KpnI EF1α fragment of pBS377, the KpnI-XbaI EGFP fragment of pEGFP-1 (Clontech, Palo Alto, Calif.) and the XbaI-EcoRI fragment from pBS377 carrying the polyA signal. The EcoRI-HindIII rox² zeo cassette from pBS1080 was blunt-end ligated into the EcoRV site lying between the EF1α promoter and the EGFP gene in pBS504 to generate the rox recombination reporter plasmid pBS1083.

DNA Analysis

A PSI-BLAST search (36) was performed to determine closest homologs of identified genes. The bendability/curvature propensity plot were calculated with the bend it server, using DNase I-based bendability parameters (37) and the consensus bendability scale (38).

Site-Specific DNA Excision

Plasmids pBAD33, pBAD33-dre or pBAD33-cre were electroporated into DH5αcells containing either the reporter plasmid pBS890 or pBS1080, incubated for 1 hr at 37° C. in SOB media (6) and then plated, selecting for Cm$^R$ Ap$^R$ to ensure retention of both plasmids in the resulting transformants. To ensure that recombinase was not expressed at inordinately high levels the pBAD plasmids were used without overt arabinose induction (9). The next day colonies were individually tested for drug resistance markers by growth on appropriate antibiotic containing plates.

CHO-K1 cells were transfected using Polyfect (Qiagen, Valencia, Calif.) with 1.5 µg DNA per well of a 6-well dish as recommended by the manufacturer. Co-transfections used a 9:1 ratio of Cre, Dre or lacZ expression vector DNA to either pBS504 or pBS1083 as indicated. Fluorescence was monitored 2 days after transfection with a Leica DMR microscope mounted with an Optronics Magnafire digital camera, and DNA was then prepared for PCR analysis. Recombination was detected by PCR (31 cycles 30 s 94° C., 30 s 60° C., 60 s 72° C.) using the sense EF1 α primer KC315 5' GCTTG-GCACTTGATGTAATTCTCCTTG 3' (SEQ ID NO. 15) and the antisense EGFP primer BSBS382 5' GGTCAGCTTGC-CGTAGGTGGC 3'(SEQ ID NO. 16). Predicted product sizes are 302 bp for pBS504, 1704 bp for pBS1083 (not observed because of the short cycling times used) and 389 bp for the Dre excision product of pBS1083.

Example 1

A comparison was performed of genes from Cre homologues. Even though the immC region of phage P1 does not cross-hybridize to phage D6 DNA it seemed likely that D6 would carry a site-specific DNA recombination system like that of P1, and that this recombinase/recombinase recognition site would lie in the D6 immC region. Presence of a recombinase activity was checked genetically. If there were a Cre-like D6 recombinase, then infection of the D6 clone plasmid library with phage D6 would identify relevant plasmid clones as a result of low level site-specific integrative recombination between phage DNA and plasmids carrying a D6 recombination site. Thus, D6 would be able to transduce relevant Ap$^R$ clones to a new bacterial recipient where they would be excised from the phage genome by the D6 site-specific recombinase to take up plasmid residency. A similar strategy was used previously to pick-up rox plasmid clones using phage lambda carrying the rox-cre region of P1 (39). Table 2 shows that D6 could transduce the Ap$^R$ marker from a library of D6 clones, but not from a strain having an anonymous randomly chosen D6 cloned insert or from a non-plasmid strain, Sh-16. These results indicate that, like P1, D6 carries a site-specific DNA recombinase that catalyzes both integrative and excisive recombination.

To compare the recombinase genes, as well as the adjacent c1 and pac genes, the ~7 kb immC region from four P1-related phages: P7 c1.9, φw39, p15B and D6 was sequenced. For the first three of these phages the gene organization of this region was identical to that of phage P1. That of phage D6 had a similar structure (FIG. 1). To confirm that this D6 region did indeed harbor the recombinase site that was detected previously, 6 randomly chosen plasmids transduced by D6 were sequenced, naming them Pick-Up clones PU-5, etc. All carried overlapping sequences from the same immC DNA region was sequenced (FIG. 1), strongly indicating that each carried a D6 DNA site for site-specific recombination.

The overall gene organization of the sequenced region from D6 is similar to the pac-ref region of P1 despite low sequence identity. On the left (FIG. 1) there is a gene showing 24% similarity to P1's lpa (late promoter activating protein) or gene 10. This is followed by DNA packaging genes (pacA and pacB), a c1 repressor gene and a D6 recombinase "dre" similar to the P1 cre gene. There are also several non-conserved ORFs in this region of the D6 genome, and an insertion of a gene similar to the deoxyuridine 5'-triphosphate nucleotidohydrolase of the photosynthetic bacterium *Rubrivivax gelatinosus* (dut; FIG. 1).

Example 2

P1 packages its DNA using a terminase composed of the PacA small subunit and the PacB large subunit. Table 3 compares the PacA's and PacB's for each of the 5 P1 family phages. Although PacA was very similar (97-100%) for phages P1, P7, φw39 and p15B, the PacA protein of D6 was 57 amino acids longer and showed only 18% similarity to PacA from any of the other phages. D6 PacB was somewhat more similar to the PacB proteins of the other P1 family members (53-54%) and was slightly larger. Interestingly, the other four phages form two clear subgroups: P1 and P7 are nearly identical to each other, likewise φw39 and p15B are nearly identical, with the two subgroups 89% similar to each other. In addition, the defective phage p15B carried a nonsense mutation that truncates the C-terminus of PacB.

Figure 3:
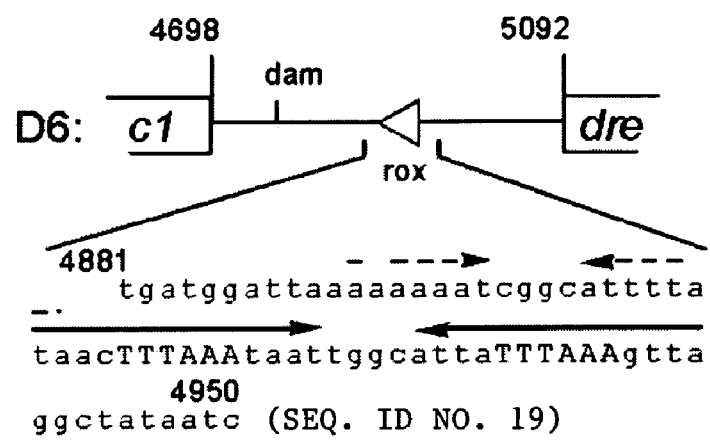
FIG. 3 depicts a schematic of the D6 c1-dre integenic region. The 394 bp region from D6 between c1 and dre is diagrammed along with the single dam site of this region. The sequence shown is a 70 bp portion of this region suspected to include the D6 rox site because of the presence of inverted repeat elements. Repeat elements of a DNA sequence shown not to be the recombination site are indicated by dashed arrows, the repeat elements of the actual rox site are indicated by solid arrows. The two DraI sites are shown in upper case.
Figure 4:
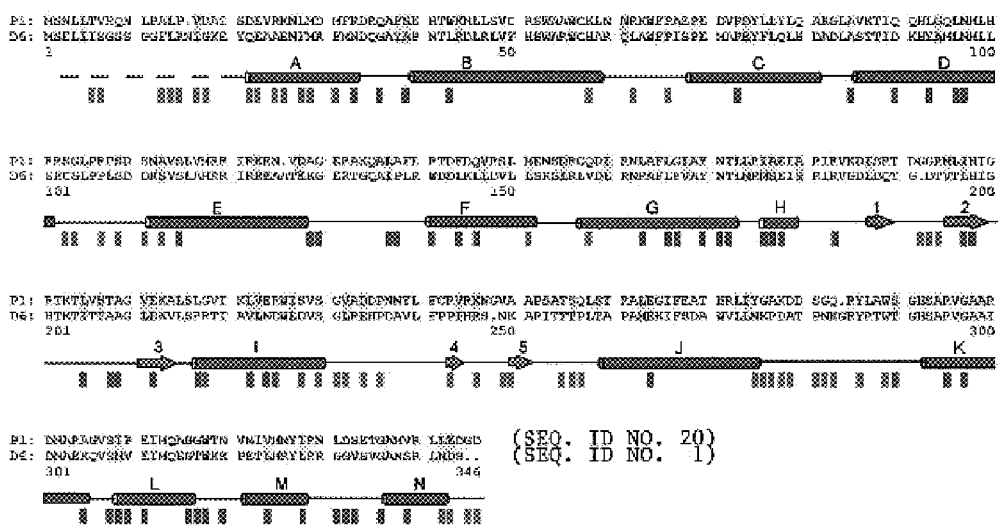
FIG. 4 depicts a schematic comparing P1 Cre and D6 Dre. Sequence identity is shown in yellow, conserved amino acid changes are shown in green. Below the sequences the known secondary structure (α-helices as dark blue cylinders, β-strands as orange arrows) of Cre is shown (50). Below the depiction of Cre secondary structure is a functional map of Cre based on pentapeptide insertion (9): blue bars represent points of insertion which have little or no effect on recombinase activity, red bars indicate points at which insertion abolishes recombinase activity.

P1 headful DNA packaging proceeds from a specific 162 bp pac site located within the 5' end of the pacA structural gene (FIG. 3). The site consists of two clusters of hexanucleotide repeats flanking a central region where DNA cleavage occurs (40). Each of the hexamer repeats has a core 5'-GATC dam methylation site. PacA protein binds to the hexamer repeats in a DNA methylation-dependent manner and then associates with PacB to loop the two binding domains in an IHF and HU-dependent manner prior to DNA cleavage (41, 42). In phages P7, φw39 and p15B this 162 bp region differed from that of P1 by 4, 9 and 2 bp, respectively, but the integrity of the seven hexamer repeats was completely preserved, suggesting that all four of these phages package DNA in the a similar manner. Similarly, the IHF binding site adjacent to the region of DNA cleavage was identical in φw39 and P1, although in P7 and p15B this site displayed a one nucleotide change from 5'-AAACAAAGAGTTA (SEQ ID NO. 17) to 5'-AAACAGAGAGTTA (SEQ ID NO. 18) (change underlined).

The low degree of similarity between D6 and P1 PacA proteins suggests that their DNA binding specificities may differ. In addition there was no region of clustered dam sites characteristic of the P1 pac site and no consensus IHF binding site in the D6 pacA gene (FIG. 3), further suggesting a difference in the DNA recognition specificities of the P1 and D6 terminases. Interestingly, though, there was a potentially curved DNA sequence in the 5' region off the D6 pacA gene (asterisk, FIG. 3). The curvature-propensity plot, calculated with DNase I-based trinucleotide parameters, contained one peculiar maximum in this region, whose magnitude (14.7°/helical turn) exceeded the value calculated for *Columba risoria* bent satellite DNA (13.5°/helical turn). No such potentially curved DNA was detected in the pacA genes of P1, P7, φw39 or p15B.

Example 3

The C1 repressor and immunity genes were examined for each phage. There was little difference in the immunity genes of the immC region for the four phages P1, P7, φw39 and p15B (FIG. 1). The C1 repressors of P1 and P7 had previously been shown to be identical (43), so the three amino acid changes (A110V, P190L and D277S) in P7 c1.9 are likely specific to this P7 temperature-sensitive repressor. Aside from a K268R change in φw39, the p15B and φw39 C1 repressors were identical to that of P1. The Coi (c one inactivator) protein sequence was identical for all four of these phages except for an A62T substitution in p15B. The predicted imcA and imcB gene products were also identical except for an A27T difference in P1. Interestingly these two genes were fused in P7. Some variation was seen for C8 among phages P1, P7, φw39 and p15B but all showed ≧85% similarity. On the other hand, the D6 C1 protein was only 16% similar to P1 C1. Moreover, in phage D6 the distance between c1 and the recombinase gene dre was much shorter than the corresponding region in P1, and the coi and imcA/imcB genes were missing.

Example 4

Dre and Cre homologue recombination activity was examined. Among the four phages P1, P7, φw39 and p15B the 343 amino acid Cre recombinase was highly conserved (FIG. 1). The φw39 Cre differed from P1 Cre by the single amino acid change T206A, P7 Cre differed from P1 Cre by the two changes A178S and G280D, and the p15B Cre differed from P1 Cre by three changes: P107L, A249S and A252P. Similarly conserved among these four phages was cra (putative cre associated function), an open reading frame of unknown function adjacent to cre originally designated orfl (44). The putative P1 Cra protein differed from that of P7, φw39 and p15B by 3, 1 and 2 amino acids respectively. In accord with the nearly identical Cre recombinases of these four phages all of them carried an identical 34 bp rox site located midway between c1 and cre.

In contrast, D6 displayed a recombinase gene only 39% similar to the P1 cre gene and no 34 bp rox site anywhere in this 7.6 kb region of DNA (FIG. 1). This suggested that the D6 recombinase (dre) might recognize a recombination site distinct from rox. As noted above, the interval between c1 and dre was much shorter in D6 than the corresponding region in P1, and no open reading frame corresponding to cra was found. From the D6 pick-up experiments it was deduced that a recombination site must lie within the D6 sequence present in the PU7 clone (FIG. 1), a 2.1 kb fragment that includes both dre and the interval between c1 and dre.

The P1 rox site consists of two 13 bp inverted repeats flanking an asymmetrical 8 bp spacer region that imparts an overall directionality to the recombination site. In the c1-dre interval from D6 two DNA sequences were detected resembling this structure. FIG. 3 shows a 69 bp portion of the c1-dre interval within which is a 32 bp sequence having two perfect 14 bp inverted repeats (solid arrows) separated by 4 bp. Just abutting this potential Dre recombination site was a similarly configured 18 bp DNA sequence with less perfect inverted repeats (dashed line arrows).

To determine the involvement of either of these DNA sequences in Dre-mediated recombination several test plasmids were constructed and evaluated for their ability to recombine with D6 using the D6 plasmid transduction assay. Table 4 shows that D6 transduces PU7, but not pUC19, from a recA host to a recA recipient at high frequency. Taking advantage of a fortuitous DraI site present in each 14 bp inverted repeat (FIG. 3, lower case) the 32 bp candidate site was mutated by deleting the 12 bp between the DraI sites site to generate a PU7 derivative, PU7-ΔDra1. The lack of D6 transduction of this plasmid (Table 4) indicated that the integrity of the 32 bp region was necessary for recombination and suggested that the adjacent shorter imperfect inverted repeat region was not a recombination site. The 32 bp region might thus be the region of crossover (X-over) recombination or rox site for Dre recombinase. To test this sequence was placed on pUC19 and tested for its ability to undergo recombination with D6. Transduction of pUC19 carrying the putative rox site occurred at high frequency (Table 4), confirming that the rox sequence was sufficient for recombination. Moreover, no transduction of a pUC19-rox plasmid was obtained, indicating that D6 can not recombine with the P1 rox site.

Figure 5:
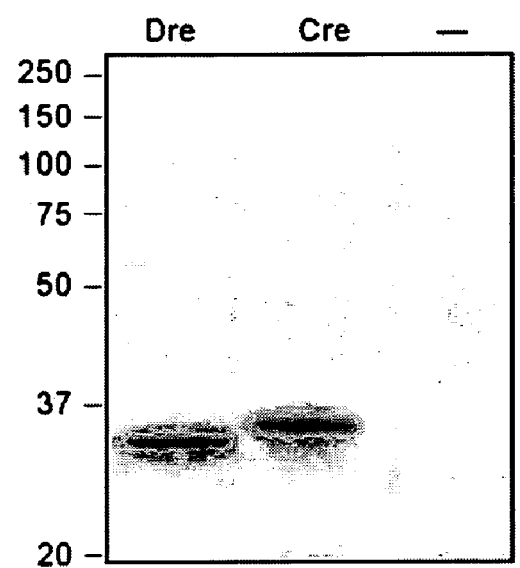
FIG. 5 is a photographic image depicting western blot detection of Dre recombinase. Size markers in kDa are shown to the right.

To establish whether the Dre recombinase was the only D6-encoded protein required for recombination at rox, as a first step in this direction, the dre structural gene was placed under the control of the arabinose-inducible promoter in plasmid pBAD33. SDS-PAGE and Western blot analysis showed that this construct expressed a Cre-sized protein of ~36 kDa that cross-reacted with a polyclonal antibody to Cre (FIG. 5).

Figure 6:
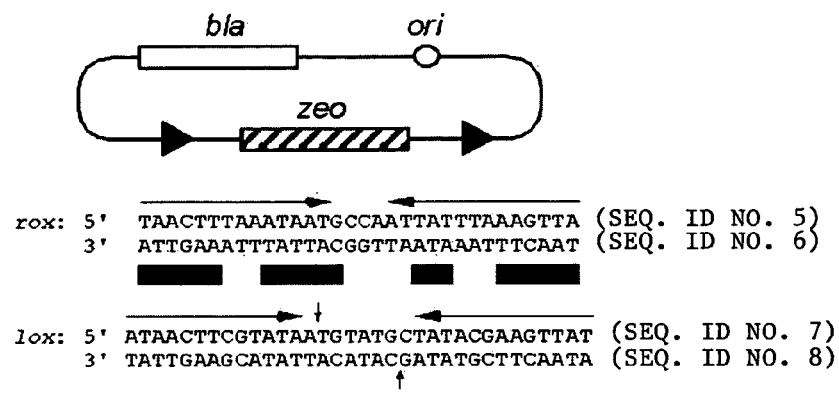
FIG. 6 is a schematic illustrating recombinase-mediated excision. Reporter plasmids were constructed by placing the zeo gene (diagonal bars) between two identical directly repeated recombination sites (black triangles). Shown are the sequences of the 32 bp rox site and the 34 bp loxP site. Horizontal arrows indicate the inverted repeat elements; positions of nucleotide identity between rox and loxP are indicated by the black boxes; and vertical arrows show the sites of Cre cleavage that define the 6 bp overlap region of the lox site.

Dre-mediated recombination was assayed using a $rox^2$ zeo construct (FIG. 6) that carries two directly repeated rox sites flanking zeo, a gene that confers resistance to the antibiotic zeocin. Cells carrying this construct become sensitive to zeocin upon loss of zeo by excisive recombination at the rox sites. Table 5 shows that transformation of the $rox^2$ zeo strain with the compatible $Cm^R$ plasmid pBAD33-dre resulted in loss of zeocin resistance in all transformants. No loss of zeo was seen with a control plasmid having no insert or with a construct expressing Cre recombinase. Conversely, a strain carrying a $rox^2$ zeo construct was refractory to excisive recombination by the Dre-expressing construct but readily underwent excisive recombination with loss of zeo when tranformed with the Cre-expressing construct. Sequencing of the rox plasmid from several zeocin sensitive colonies confirmed that precise excisive recombination had occurred at the rox site. Thus Dre mimicked Cre's ability to perform excisive recombination but the two recombinases were heterospecific, that is, Cre did not catalyze recombination at rox and Dre did not catalyze recombination at rox.

Figure 7:
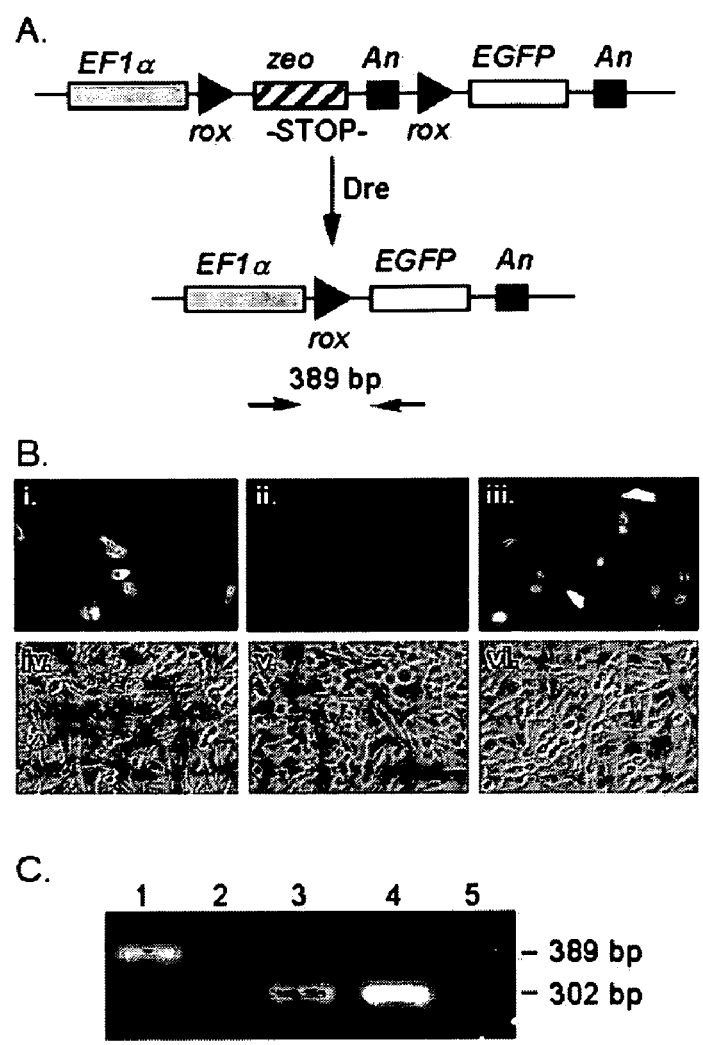
FIG. 7A depicts a schematic illustrating recombination activation of gene expression by Dre. Expression of the EGFP gene from the EF1α promoter in the reporter plasmid pBS1083 is blocked by the interposed zeo gene and polyadenylation site (An). Dre-mediated recombination at the flanking rox sites (black triangles) removes this "STOP" signal to allow EGFP expression. Horizontal arrows indicate the PCR primers used to produce the 389 bp fragment diagnostic of recombination.
FIG. 7B is a photographic image depicting activation of EGFP expression by Dre. Epifluorescence (panels i-iii) and differential interference contrast (panels iv-vi) images of CHO cells 36 h after DNA transfection. Panels i and iv show Dre expression plasmid pBS1081+the $rox^2$ STOP EGFP plasmid pBS 1083; panels ii and v show Cre expression plasmid pBS513+pBS 1083; panels iii and vi show control lacZ plasmid p324+the EGFP plasmid pBS504.
FIG. 7C is a photographic image detailing PCR detection of recombination. DNA from the transfected CHO cells shown in panel B was amplified using the primers shown in panel A. The following materials were placed in the lanes; lane 1: CHO cells transfected with the Dre expression plasmid pBS1081+the $rox^2$ STOP EGFP plasmid pBS 1083; lane 2: CHO cells transfected with the Cre expression plasmid pBS513+pBS1083; lane 3: CHO cells transfected with the control lacZ plasmid p324+the EGFP plasmid pBS504; lane 4: EGFP plasmid pBS504; lane 5: $rox^2$ STOP EGFP plasmid pBS1083.

Unlike many members of the tyrosine recombinase family, Cre recombinase of phage P1 requires no accessory phage or bacterial proteins for recombination. This characteristic of Cre is illustrated by Cre's ability to catalyze DNA recombination in a variety of eukaryotic cells (45,46). To determine whether Dre also had no requirement for accessory bacterial proteins, and thus would be able to catalyze DNA recombination in a mammalian cell, Dre's ability to recombine rox sites in CHO cells was tested. Dre recombination was assayed by using a reporter plasmid that would express EGFP in transfected cells only if activated by recombination between two directly repeated rox sites (FIG. 7A). In the reporter plasmid a $rox^2$ zeo cassette is inserted between the EF1α promoter and the EGFP gene, positioning both an upstream zeo gene and a polyadenylation site act to block EGFP expression. Dre-mediated recombination at the flanking rox sites would remove these blocks. To express Dre, a second plasmid vector was constructed in which the dre gene was placed under the control of the EF1α promoter. FIG. 7B shows that co-transfection of CHO cells with the rox reporter construct and the Dre expression vector produced a significant number of green fluorescent cells (panel i), whereas there was no detectable fluorescence was when the reporter was co-transfected with a Cre expression plasmid (panel ii). he frequency of fluorescent cells from Dre-mediated activation of the EGFP gene was similar to the transfection efficiency of an EGFP reporter plasmid having no $rox^2$ zeo cassette (panel iii). PCR confirmed that recombination at the rox sites in cells co-transfected with the Dre expression plasmid and that no recombination occurred at the rox sites in cells co-transfected with the Cre expression plasmid (FIG. 7C). Thus, Dre-mediated recombination requires no bacterial proteins for efficient DNA recombination at rox.

The tables referenced in the examples are shown below.

TABLE 1

Bacterial strains

| Strain | Relevant Genotype | Source/Description |
|---|---|---|
| Sh-16 (*Shigella dysenteriae*) | $Str^R$ | J. Scott (52) |
| *Escherichia coli*: | | |
| DH5ΔlacU169 | recA lacU169 | M. Berman |
| DH5α | recA lacU169 (φ80dlacΔM15) | Invitrogen |
| BS610 | DH5ΔlacU169 (P1 CM r⁻ m⁻) | this work |
| BR231 | (P7 c1.9) | M. Yarmolinsky (53) |
| 39W (CCUG#11425) | (φw39) | Univ. of Göteborg, Sweden (22) |
| 15 (CGSC#4905) | (p15B) | *E. coli* Genetic Stock Center (21) |
| C600(D6) | (D6) | J. Scott (25) |
| BS1379 | DH5α [pBS516] | this work/rox plasmid |
| BS1478 | DH5α [pUC19] | this work |
| BS2060 | DH5α [pBS1051] | this work/rox plasmid |
| BS2061 | DH5α [PU-7] | this work |
| BS2080 | DH5α [PU-7 ΔDra] | this work |
| BS2089 | DH5α [pBS1080] | this work/pUC-$rox^2$-zeo |
| BS1850 | DH5α [pBS890] | this work/pUC-$rox^2$-zeo |

TABLE 2

D6 "pick-up" identification of a D6 recombination site

| D6 Transducing stock | $Ap^R$ colonies | Frequency ($Ap^R$/pfu) |
|---|---|---|
| D6.Sh-16 | 0 | $<2.5 \times 10^{-8}$ |
| D6.Lib1000[a] | 32 | $1.7 \times 10^{-5}$ |
| D6.clone#3[b] | 0 | $<8.3 \times 10^{-7}$ |

[a] The donor strain was a pool of 1000 colonies from the EcoRI-sized D6 library.
[b] The donor strain was a randomly chosen clone from the EcoRI-sized D6 library.

TABLE 3

DNA packaging genes

| | | Similarity | | | | |
|---|---|---|---|---|---|---|
| Protein/phage | Size (aa) | P1 | P7 | φw39 | p15B | D6 |
| PacA | | | | | | |
| P1 | 397 | 100 | 99 | 96 | 97 | 18 |
| P7 | 397 | | 100 | 96 | 97 | 18 |
| φw39 | 397 | | | 100 | 98 | 18 |
| p15B | 397 | | | | 100 | 18 |
| D6 | 454 | | | | | 100 |
| PacB | | | | | | |
| P1 | 494 | 100 | 100 | 89 | 89 | 53 |
| P7 | 494 | | 100 | 89 | 89 | 53 |
| φw39 | 494 | | | 100 | 100 | 54 |
| p15B | 494* | | | | 100 | 54 |
| D6 | 502 | | | | | 100 |

*Amber mutation at aa position 473.

TABLE 4

Plasmid transduction by phage D6

| Plasmid (donor strain) | D6 Transduction Frequency ($Ap^R$/pfu) |
|---|---|
| pUC19 | <0.00004 |
| PU7 | 0.08 |
| PU7-ΔDra | <0.001 |
| pUC-rox | 0.09 |
| pUC-rox | <0.00004 |

TABLE 5

Dre-mediated excision in *E. coli*

| | Resident Reporter | Transformants tested | | | |
|---|---|---|---|---|---|
| Plasmid | Construct | $Cm^R$ | $Ap^R$ | $Zeo^R$ | % Excision |
| pBAD33 | $rox^2$ zeo | 152 | | 152 | 0 |
| pBAD33-dre | $rox^2$ zeo | 152 | | 0 | 100 |
| pBAD33-cre | $rox^2$ zeo | 152 | | 152 | 0 |
| pBAD33 | $rox^2$ zeo | 152 | | 152 | 0 |
| pBAD33-dre | $rox^2$ zeo | 152 | | 152 | 0 |
| pBAD33-cre | $rox^2$ zeo | 152 | | 0 | 100 |

CONCLUSION

Comparison of the pac-c1 regions of P1 and four other P1-related phages showed that the gene organization of this region is conserved, and that the gene products of this region are nearly identical for all phages with the exception of D6. From sequence comparisons the specificity of the D6 DNA packaging, immunity and site-specific DNA recombinase functions are likely to be different from those of P1. The heterospecificity for the DNA recombinase Dre of D6 has been confirmed and it has also been shown that Dre can catalyze site-specific DNA recombination in mammalian cells.

All references cited in the preceding text of the patent application or in the following reference list, to the extent that they provide exemplary, procedural, or other details supplementary to those set forth herein, are specifically incorporated by reference to the same extent as if each individual publication or patent application was specifically and individually indicated to be incorporated by reference.

REFERENCES

1. Van Duyne, G. D. (2002) A structural view of tyrosine recombinase site-specific recombination. In Craig, N. L., Craigie, R., Gellert, M. and Lambowitz, A. M. (eds.), *Mobile DNA II*. ASM Press, Washington, D.C., pp. 93-117.
2. Sauer, B. (2002) Chromosome manipulation by Cre-rox recombination. In Craig, N. L., Craigie, R., Gellert, M. and Lambowitz, A. M. (eds.), *Mobile DNA II*. ASM Press, Washington, D.C., pp. 38-58.
3. Wierzbicki, A., Kendall, M., Abremski, K. and Hoess, R. (1987) A mutational analysis of the bacteriophage P1 recombinase Cre. *J. Mol. Biol.*, 195, 785-794.
4. Buchholz, F. and Stewart, A. F. (2001) Alteration of Cre recombinase site specificity by substrate-linked protein evolution. *Nat. Biotechnol.*, 19, 1047-1052.
5. Santoro, S. W. and Schultz, P. G. (2002) Directed evolution of the site specificity of Cre recombinase. *Proc. Natl. Acad. Sci. USA*, 99, 4185-4190.
6. Rüfer, A. W. and Sauer, B. (2002) Non-contact positions impose site selectivity on Cre recombinase. *Nucleic Acids Res.*, 30, 2764-2771.
7. Argos, P., Landy, A., Abremski, K., Egan, J. B., Ljungquist, E. H., Hoess, R. H., Kahn, M. L., Kalionis, B., Narayana, S. V. L., Pierson, L. S. et al. (1986) The integrase family of site-specific recombinases: regional similarities and global diversity. *EMBO J.*, 5, 433-440.
8. Swalla, B. M., Gumport, R. I. and Gardner, J. F. (2003) Conservation of structure and function among tyrosine recombinases: homology-based modeling of the lambda integrase core-binding domain. *Nucleic Acids Res*, 31, 805-818.
9. Petyuk, V., McDermott, J., Cook, M. and Sauer, B. (2004) Functional mapping of Cre recombinase by pentapeptide insertional mutagenesis. *J Biol Chem*, 279, 37040-37048.
10. Dorgai, L., Yagil, E. and Weisberg, R. A. (1995) Identifying determinants of recombination specificity: construction and characterization of mutant bacteriophage integrases. *J Mol Biol*, 252, 178-188.
11. Yagil, E., Dorgai, L. and Weisberg, R. A. (1995) Identifying determinants of recombination specificity: construction and characterization of chimeric bacteriophage integrases. *J Mol Biol*, 252, 163-177.
12. Labocka, M. B., Rose, D. J., Plunkett III, G., Rusin, M., Samojedny, A., Lehnherr, H., Yarmolinsky, M. and Blattner, F. R. (2004) The genome of bacteriophage P1. *J. Bacteriol.*, in press.
13. Austin, S., Ziese, M. and Sternberg, N. (1981) A novel role for site-specific recombination in maintenance of bacterial replicons. *Cell*, 25, 729-736.
14. Sternberg, N. L. and Maurer, R. (1991) Bacteriophage-mediated generalized transduction in *Escherichia coli* and *Salmonella typhimurium*. *Methods Enzymol*, 204, 18-43.
15. Sternberg, N. (1990) Bacteriophage P1 cloning system for the isolation, amplification, and recovery of DNA fragments as large as 100 kilobase pairs. *Proc. Natl. Acad. Sci. USA*, 87, 103-107.
16. Heinrich, J., Velleman, M. and Schuster, H. (1995) The tripartite immunity system of phages P1 and P7. *FEMS Microbiol Rev*, 17, 121-126.
17. Eliason, J. L. and Sternberg, N. (1987) Characterization of the binding sites of c1 repressor of bacteriophage P1. Evidence for multiple asymmetric sites. *J Mol Biol*, 198, 281-293.
18. Laufer, C. S., Hays, J. B., Windle, B. E., Schaefer, T. S., Lee, E. H., Hays, S. L. and McClure, M. R. (1989) Enhancement of *Escherichia coli* plasmid and chromosomal recombination by the Ref function of bacteriophage P1. *Genetics*, 123, 465-476.
19. Lu, S. D., Lu, D. and Gottesman, M. (1989) Stimulation of IS1 excision by bacteriophage P1 ref function. *J Bacteriol*, 171, 3427-3432.
20. Smith, H. W. (1972) Ampicillin resistance in *Escherichia coli* by phage infection. *Nat New Biol*, 238, 205-206.
21. Ikeda, H., Inuzuka, M. and Tomizawa, J. I. (1970) P1-like plasmid in *Escherichia coli* 15. *J Mol Biol*, 50, 457-470.
22. Yoshida, Y. and Mise, K. (1984) Characterization of generalized transducing phage φw39 heteroimmune to phage P1 in *Escherichia coli* W39. *Microbiol Immunol*, 28, 415-426.
23. Mise, K. and Suzuki, K. (1970) New generalized transducing bacteriophage in *Escherichia coli*. *J Virol*, 6, 253-255.
24. Meyer, J., Stalhammar-Carlemalm, M., Streiff, M., Iida, S. and Arber, W. (1986) Sequence relations among the IncY plasmid p15B, P1, and P7 prophages. *Plasmid*, 16, 81-89.
25. Watkins, C. A. and Scott, J. R. (1981) Characterization of bacteriophage D6. *Virology*, 110, 302-317.
26. Sambrook, J., Fritsch, E. F. and Maniatis, T. (1989) *Molecular Cloning: A Laboratory Manual*. Cold Spring Harbor Laboratory, Cold Spring Harbor, N.Y.
27. Lennox, E. S. (1955) Transduction of linked genetic characters of the host by bacteriophage P1. *Virology*, 1, 190-206.
28. Wall, J. D. and Harriman, P. D. (1974) Phage P1 mutants with altered transducing abilities for *Escherichia coli*. *Virology*, 59, 532-544.
29. Sauer, B., Whealy, M., Robbins, A. and Enquist, L. (1987) Site-specific insertion of DNA into a pseudorabies virus vector. *Proc. Natl. Acad. Sci. USA*, 84, 9108-9112.
30. Sauer, B. (1993) Manipulation of the transgene by site-specific recombination: use of the cre recombinase. *Meth. Enzymol.*, 225, 890-900.
31. Guzman, L.-M., Belin, D., Carson, M. J. and Beckwith, J. (1995) Tight regulation, modulation, and high-level expression by vectors containing the arabinose pBAD promoter. *J. Bacteriol.*, 177, 4121-4130.
32. Gagneten, S., Le, Y., Miller, J. and Sauer, B. (1997) Brief expression of a GFPcre fusion gene in embryonic stem cells allows rapid retrieval of site-specific genomic deletions. *Nucleic Acids Res.*, 25, 3326-3331.
33. Le, Y., Miller, J. L. and Sauer, B. (1999) GFPcre fusion vectors with enhanced expression. *Anal. Biochem.*, 270, 334-336.
34. Eustice, D. C., Feldman, P. A., Colberg-Poley, A. M., Buckery, R. M. and Neubauer, R. H. (1991) A sensitive method for the detection of β-galactosidase in transfected mammalian cells. *BioTechniques*, 11, 739-743.
35. Bethke, B. and Sauer, B. (1997) Segmental genomic replacement by Cre-mediated recombination: Genotoxic stress activation of the p53 promoter in single-copy transformants. *Nucleic Acids Res.*, 25, 2828-2834.
36. Altschul, S. F., Madden, T. L., Schaffer, A. A., Zhang, J., Zhang, Z., Miller, W. and Lipman, D. J. (1997) Gapped BLAST and PSI-BLAST: a new generation of protein database search programs. *Nucleic Acids Res*, 25, 3389-3402.
37. Brukner, I., Sanchez, R., Suck, D. and Pongor, S. (1995) Sequence-dependent bending propensity of DNA as revealed by DNase I: parameters for trinucleotides. *Embo J*, 14, 1812-1818.

38. Gabrielian, A. and Pongor, S. (1996) Correlation of intrinsic DNA curvature with DNA property periodicity. *FEBS Lett*, 393, 65-68.
39. Hoess, R. H., Ziese, M. and Sternberg, N. (1982) P1 site-specific recombination: nucleotide sequence of the recombining sites. *Proc. Natl. Acad. Sci. USA,* 79, 3398-3402.
40. Sternberg, N. and Coulby, J. (1987) Recognition and cleavage of the bacteriophage P1 packaging site (pac). II. Functional limits of pac and location of pac cleavage termini. *J Mol Biol,* 194, 469-479.
41. Skorupski, K., Sauer, B. and Sternberg, N. (1994) Faithful cleavage of the P1 packaging site (pac) requires two phage proteins, PacA and PacB, and two *Escherichia coli* proteins, 1HF and HU. *J Mol Biol,* 243, 268-282.
42. Skorupski, K., Sternberg, N. and Sauer, B. (1994) Purification and DNA-binding activity of the PacA subunit of the bacteriophage P1 pacase enzyme. *J Mol Biol,* 243, 258-267.
43. Osborne, F. A., Stovall, S. R. and Baumstark, B. R. (1989) The c1 genes of P1 and P7. *Nucleic Acids Res,* 17, 7671-7680.
44. Sternberg, N., Sauer, B., Hoess, R. and Abremski, K. (1986) Bacteriophage P1 cre gene and its regulatory region: evidence for multiple promoters and for regulation by DNA methylation. *J. Mol. Biol.,* 187, 197-212.
45. Sauer, B. (1987) Functional expression of the cre-rox site-specific recombination system in the yeast *Saccharomyces cerevisiae. Mol. Cell. Biol.,* 7, 2087-2096.
46. Sauer, B. and Henderson, N. (1988) Site-specific DNA recombination in mammalian cells by the Cre recombinase of bacteriophage P1. *Proc. Natl. Acad. Sci. USA,* 85, 5166-5170.
47. Lee, L. and Sadowski, P. D. (2003) Sequence of the rox site determines the order of strand exchange by the Cre recombinase. *J Mol Biol,* 326, 397-412.
48. Hartung, M. and Kisters-Woike, B. (1998) Cre homologues with altered DNA binding properties. *J. Biol. Chem.,* 273, 22884-22891.
49. Kim, S., Kim, G., Lee, Y. and Park, J. (2001) Characterization of Cre-rox interaction in the major groove: Hint for structural distortion of mutant Cre and possible strategy for HIV-1 therapy. *J. Cell. Biochem.,* 80, 321-327.
50. Guo, F., Gopaul, D. N. and Van Duyne, G. D. (1997) Structure of Cre recombinase complexed with DNA in a site-specific recombination synapse. *Nature,* 389, 40-46.
51. Sauer, B. (1994) Site-specific recombination: developments and applications. *Curr. Opin. Biotech.,* 5, 521-527.
52. Scott, J. R. (1968) Genetic studies on bacteriophage P1. *Virology,* 36, 564-574.
53. Wandersman, C. and Yarmolinsky, M. (1977) Bipartite control of immunity conferred by the related heteroimmune plasmid prophages, P1 and P7 (formerly phi Amp). *Virology,* 77, 386-400.

What is claimed is:

1. A purified Dre recombinase, the amino acid sequence of which comprises a sequence at least 95% identical to SEQ ID NO. 1, which recombinase catalyzes site specific recombination at a rox site.

2. The purified Dre recombinase of claim 1, the amino acid sequence of which comprises a sequence at least 99% identical to SEQ ID NO. 1, which recombinase catalyzes site specific recombination at a rox site.

3. The purified Dre recombinase of claim 1, the amino acid sequence of which comprises SEQ ID NO. 1 with 1 to 15 conservative amino acid substitutions, which recombinase catalyzes site specific recombination at a rox site.

4. The purified Dre recombinase of claim 1, the amino acid sequence of which comprises SEQ ID NO. 1 with 1 to 10 conservative amino acid substitutions, which recombinase catalyzes site specific recombination at a rox site.

5. The purified Dre recombinase of claim 1, the amino acid sequence of which comprises SEQ ID NO. 1.

6. The purified Dre recombinase of claim 1, the amino acid sequence of which consists of SEQ ID NO. 1.

7. An isolated polypeptide, the amino acid sequence of which comprises SEQ ID NO:1.

8. An isolated polypeptide, the amino acid sequence of which consists of SEQ ID NO:1.

* * * * *